(12) United States Patent
Goossens et al.

(10) Patent No.: US 12,409,159 B2
(45) Date of Patent: Sep. 9, 2025

(54) 3-HYDROXYBUTYRATE ALONE OR IN COMBINATION FOR USE IN THE TREATMENT OF CRITICAL CARE TREATMENT

(71) Applicant: KATHOLIEKE UNIVERSITEIT LEUVEN, Leuven (BE)

(72) Inventors: Chloe Christian Goossens, Sint-Michiels (BE); Lies Langouche, Leuven (BE); Greet Van Den Berghe, Grez-Doiceau (BE); Ilse Vanhorebeek, Lubbeek (BE)

(73) Assignee: Katholieke Universiteit Leuven, Leuvan (BE)

( * ) Notice: Subject to any disclaimer, the term of this patent is extended or adjusted under 35 U.S.C. 154(b) by 0 days.

(21) Appl. No.: 18/135,847

(22) Filed: Apr. 18, 2023

(65) Prior Publication Data
US 2023/0310353 A1   Oct. 5, 2023

Related U.S. Application Data

(63) Continuation of application No. 16/472,600, filed as application No. PCT/EP2017/081394 on Dec. 4, 2017, now abandoned.

(60) Provisional application No. 62/438,771, filed on Dec. 23, 2016.

(30) Foreign Application Priority Data

Aug. 1, 2017 (LU) ........................................ 100353

(51) Int. Cl.
| | | |
|---|---|---|
| *A61K 31/19* | (2006.01) | |
| *A61K 9/00* | (2006.01) | |
| *A61P 3/02* | (2006.01) | |

(52) U.S. Cl.
CPC ............ *A61K 31/19* (2013.01); *A61K 9/0029* (2013.01); *A61P 3/02* (2018.01)

(58) Field of Classification Search
CPC ................................ A61K 31/19; A61P 25/36
See application file for complete search history.

(56) References Cited

PUBLICATIONS

Aune et al., BMI and all cause mortality: systematic review and non-linear dose-response meta-analysis of 230 cohort studies with 3.74 million deaths among 30.3 million participants, BMJ May 4, 2016;353:12156.*
Dalkeith et al., The use of 3-hydroxybutyrate in patients with fat oxidation disorders, Journal of Inherited Metabolic Disease, (Sep. 2013) vol. 36, No. 2, Supp. Suppl. 1, pp. S94. Abstract No. W-013.*
Luethi et al, Prevalence of ketosis, ketonuria, and ketoacidosis during liberal glycemic control in critically ill patients with diabetes: an observational study, Critical Care (2016) 20:297.*
Olpin, Implications of impaired ketogenesis in fatty acid oxidation disorders, Prostaglandins, Leukotrienes and Essential Fatty Acids, (2004), 70(3), 293-308.*
STN document No. 2015188159, Jul. 15, 2015.*
Valayannopoulos et al., Successful Treatment of Severe Cardiomyopathy in Glycogen Storage Disease Type III With d,l-3-Hydroxybutyrate, Ketogenic and High-Protein Diet, Pediatric Research, vol. 70(6), Dec. 2011, pp. 638-641.*
Rijt et al., P-251, Journal of Inherited Metabolic Disease, vol. 37, pp. 27-185 (2014).*
Beylot et al., Metabolic effects of a D-β-hydroxybutyrate infusion in septic patients, Critical Care Medicine: Jul. 1994—vol. 22—Issue 7—p. 1091-1098.*
Kress, John P. et al., "ICU-Acquired Weakness and Recovery from Critical Illness," The New England Journal of Medicine, 2014, 370:1626-35.
Hermans, Greet et al., "Effect of tolerating macronutrient deficit on the development of intensive care unit-acquired weakness: a subanalysis of the EPaNIC trial," Lancet Respir Med, 2013, 1(8):621-9.
Derde, S. et al., "Muscle atrophy and preferential loss of myosin in prolonged critically ill patients," Crit Care Med., 2012, 40(1):79-89.
Dhainaut, Jean-Francois et al., "Coronary hemodynamics and myocardial metabolism of lactate, free fatty acids, glucose, and ketones in patients with septic shock," Circulation, 1987, 75(3):533-541.
Lanza-Jacoby, S. et al., "Altered ketone body metabolism during gram-negative sepsis in the rate," Metabolism, 1990, 39(11):1151-1157.
Shaw, J.H.F. et al., "Energy and substrate kinetics and oxidation during ketone infusion in septic dogs," Circulatory Shock, 1984, 14(1):63-79.
Wannemacher, Jr., R. W. et al., "Use of Ketogenic Substrates During Parenteral Nutrition of Septic Monkeys," Federation Proceedings, 1981, 40(3):919 (65th Annual Meeting of the Federation of American Societies for Experimental Biology, Atlanta, GA) (1 page).
Wannemacher, Robert W. et al., "Role of the liver in regulation of ketone body production during sepsis," Journal of Clinical Investigation, 1979, 64(6):1565-1572.
Levy, B. et al., "Evolution of lactate/pyruvate and arterial ketone body ratios in the early course of catecholamine-treated septic shock," Critical Care Medicine, 1999, 28(1):114-119.
Shukla, Surendra K. et al., "Metabolic reprogramming induced by ketone bodies diminishes pancreatic cancer cachexia," Cancer & Metabolism, 2014, 2:18 (19 pages).
International Search Report and Written Opinion for International App. No. PCT/EP2017/081394 dated Jun. 28, 2018.
Casaer, Michael P. et al., "Early versus Late Parenteral Nutrition in Critically Ill Adults," The New England Journal of Medicine, 2011, 365(6):506-17.

(Continued)

*Primary Examiner* — Svetlana M Ivanova
(74) *Attorney, Agent, or Firm* — K&L Gates LLP

(57) ABSTRACT

This invention relates generally to methods and compositions for the treatment or prevention of critical illness myopathy and critical illness polyneuropathy and of critical illness myopathy and critical illness polyneuropathy caused by critical illnesses including sepsis, severe sepsis, severe sepsis with septic shock, and particularly to the use of a combination of parenteral or enteral feeding with a 3-hydroxybutyrate.

9 Claims, 24 Drawing Sheets

(56) References Cited

PUBLICATIONS

Marques, Mirna B. et al., "Critical illness induces nutrient-independent adipogenesis and accumulation of alternatively activated tissue macrophages," Critical Care, 2013, 17(5):R193.

Beylot et al., Metabolic effects of a D-[3-hydroxybutyrate infusion in septic patients, Critical Care Medicine: Jul. 1994—vol. 22—Issue 7—p. 1091-1098.

Aune et al., BMI and all cause mortality: systematic review and non-linear dose-response meta-analysis of 230 cohort studies with 3.74 million deaths among 30.3 million participants, BMJ May 4, 2016;353:i2156.

\* cited by examiner

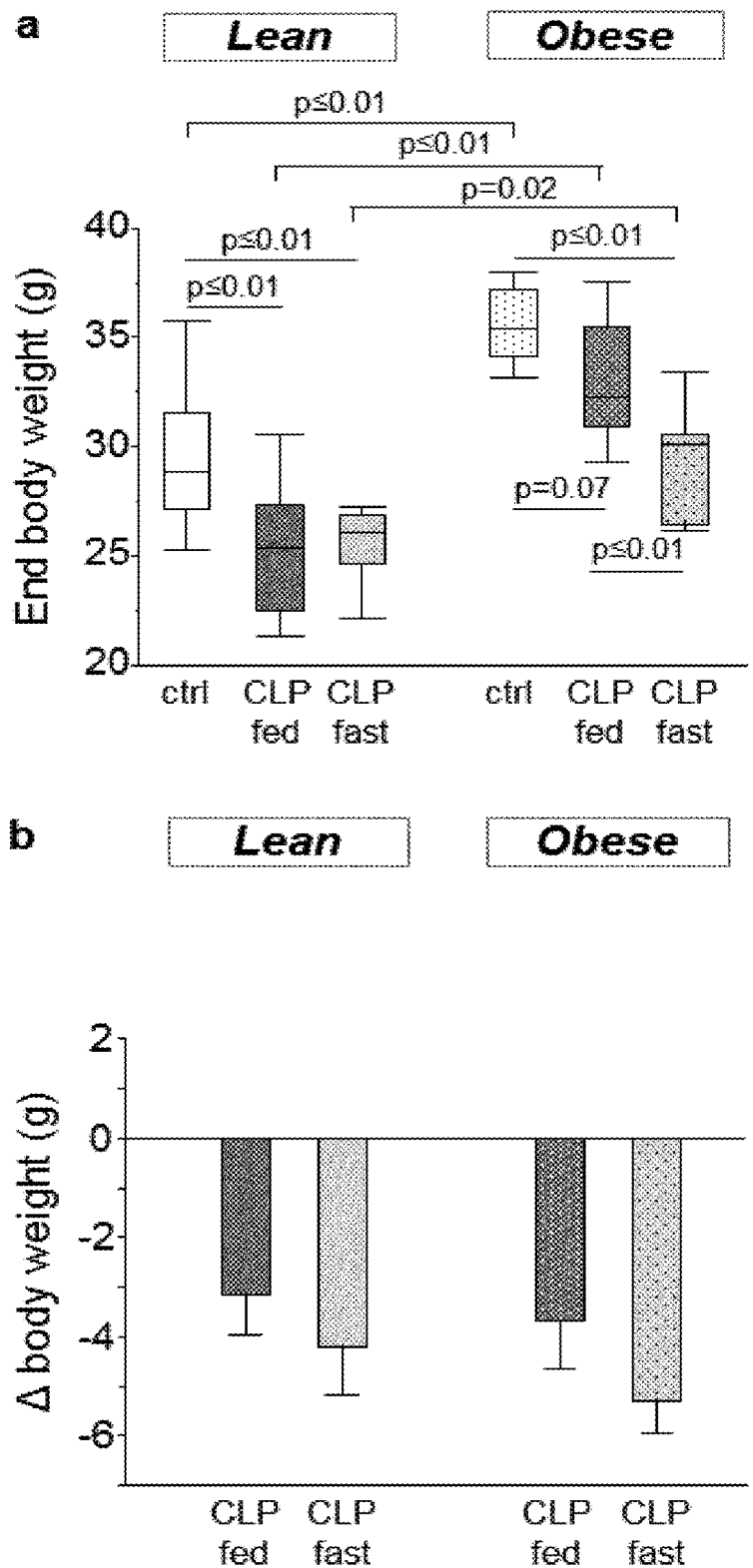
Figure 1a + 1b

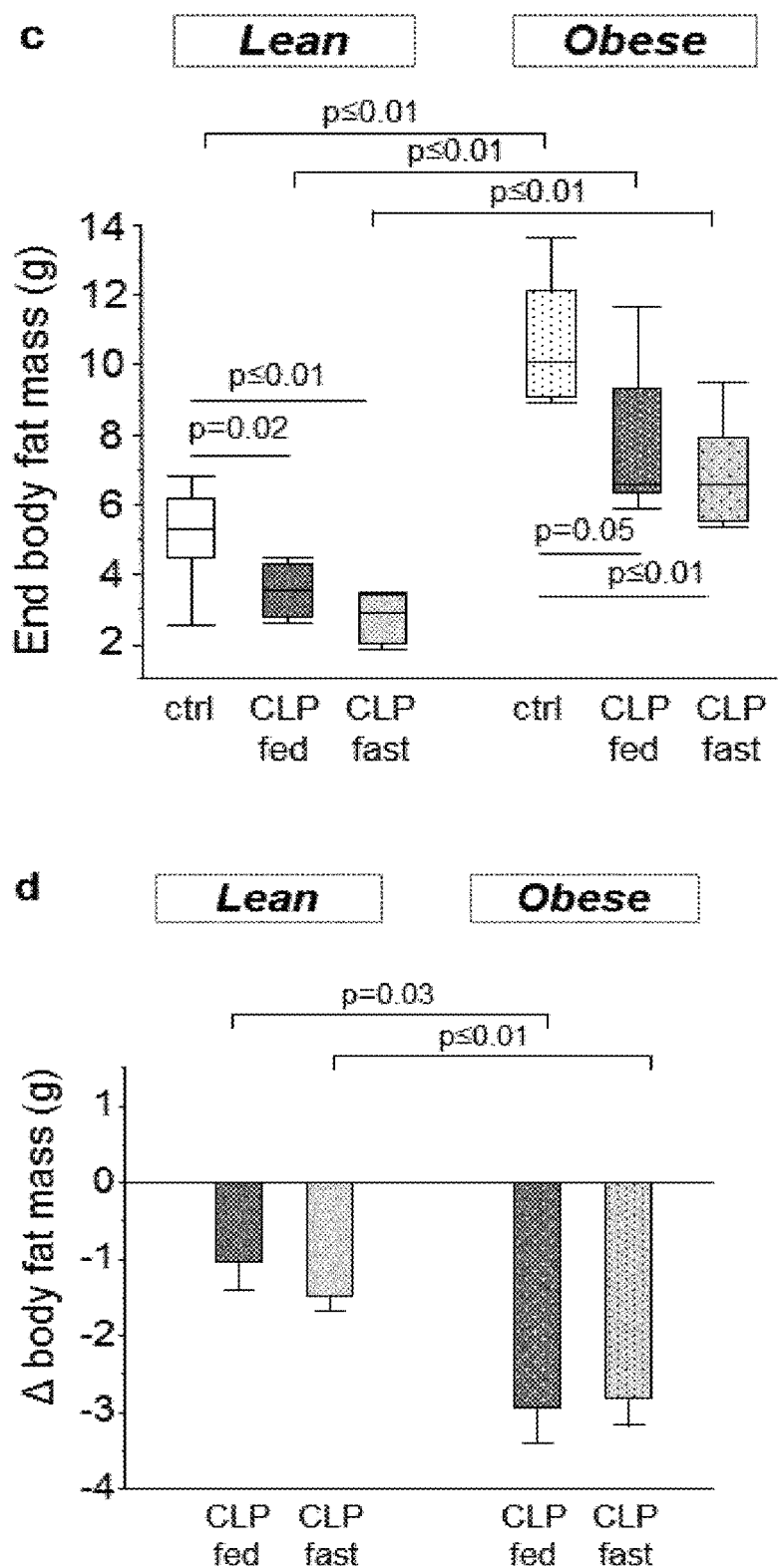
Figure 1c + 1d

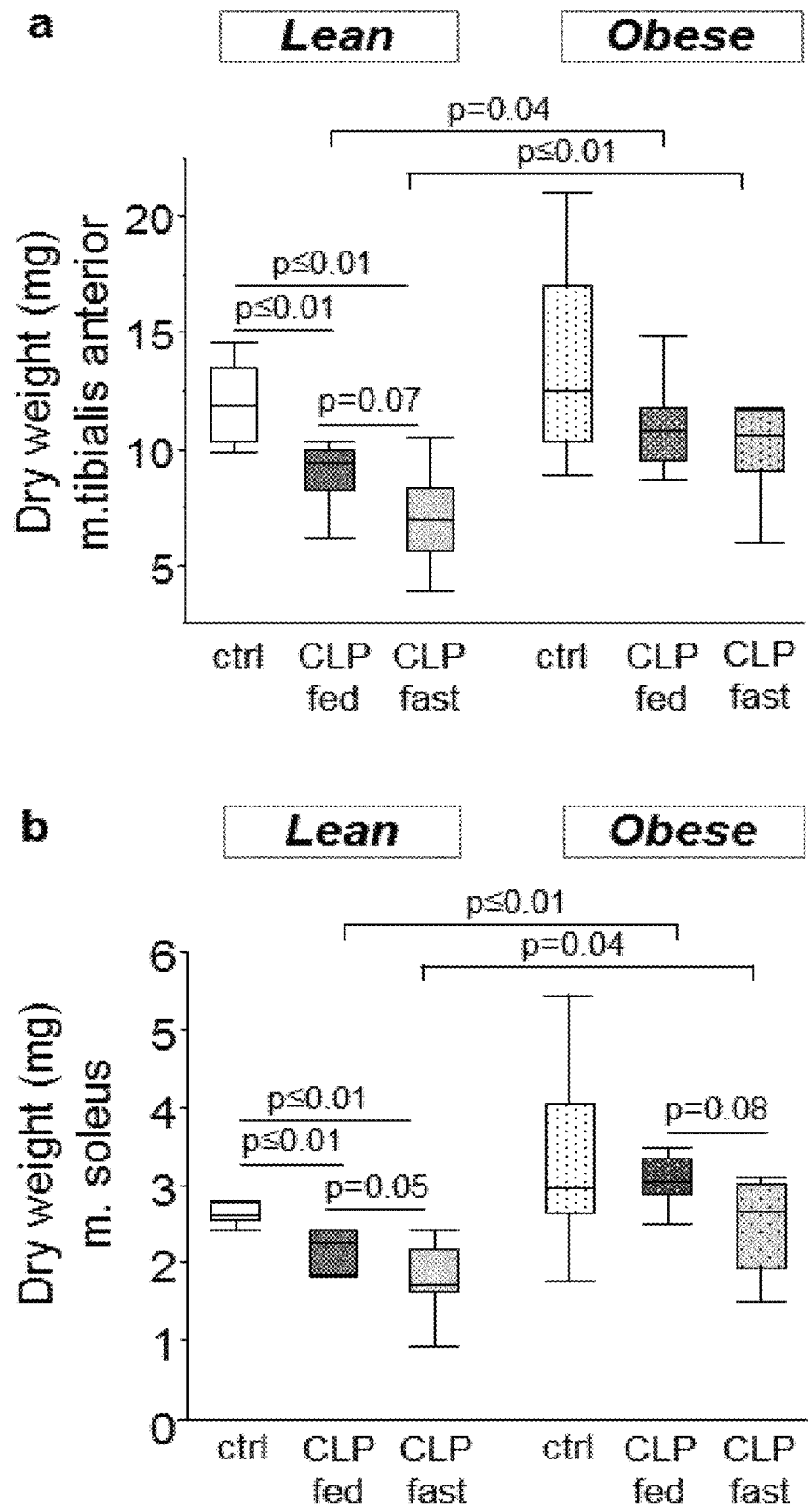
Figure 2a+ 2b

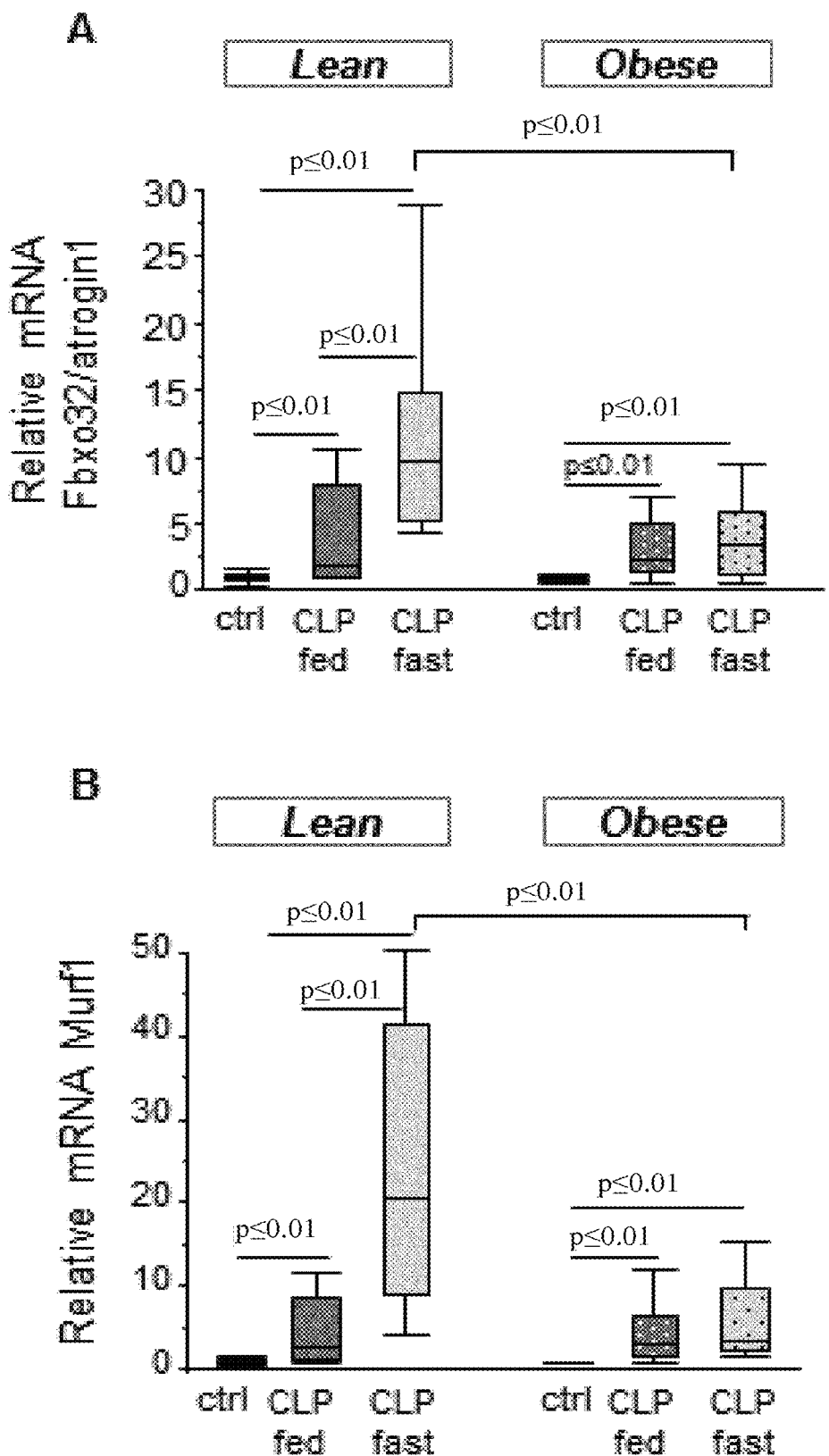
Figure 3A + 3B

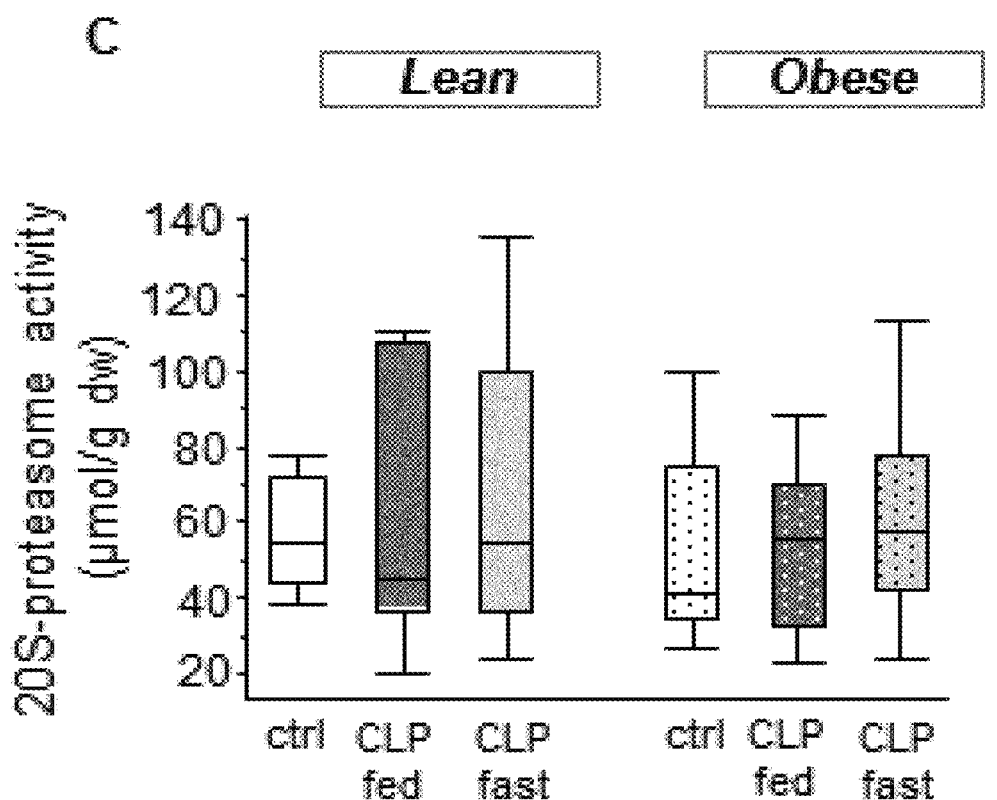
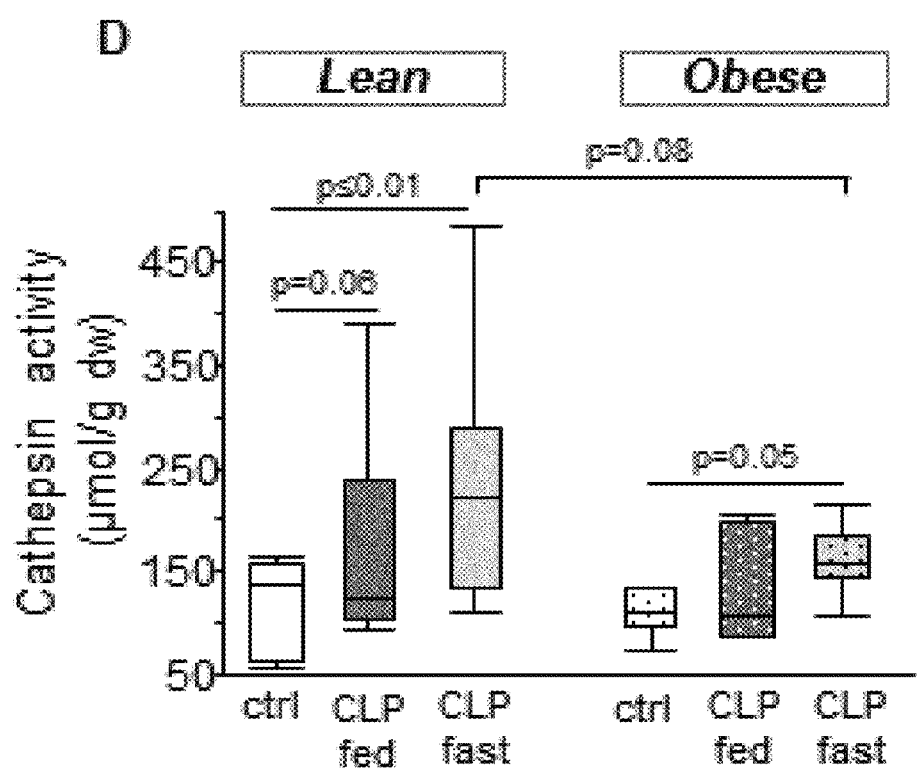
Figure 3C + 3D

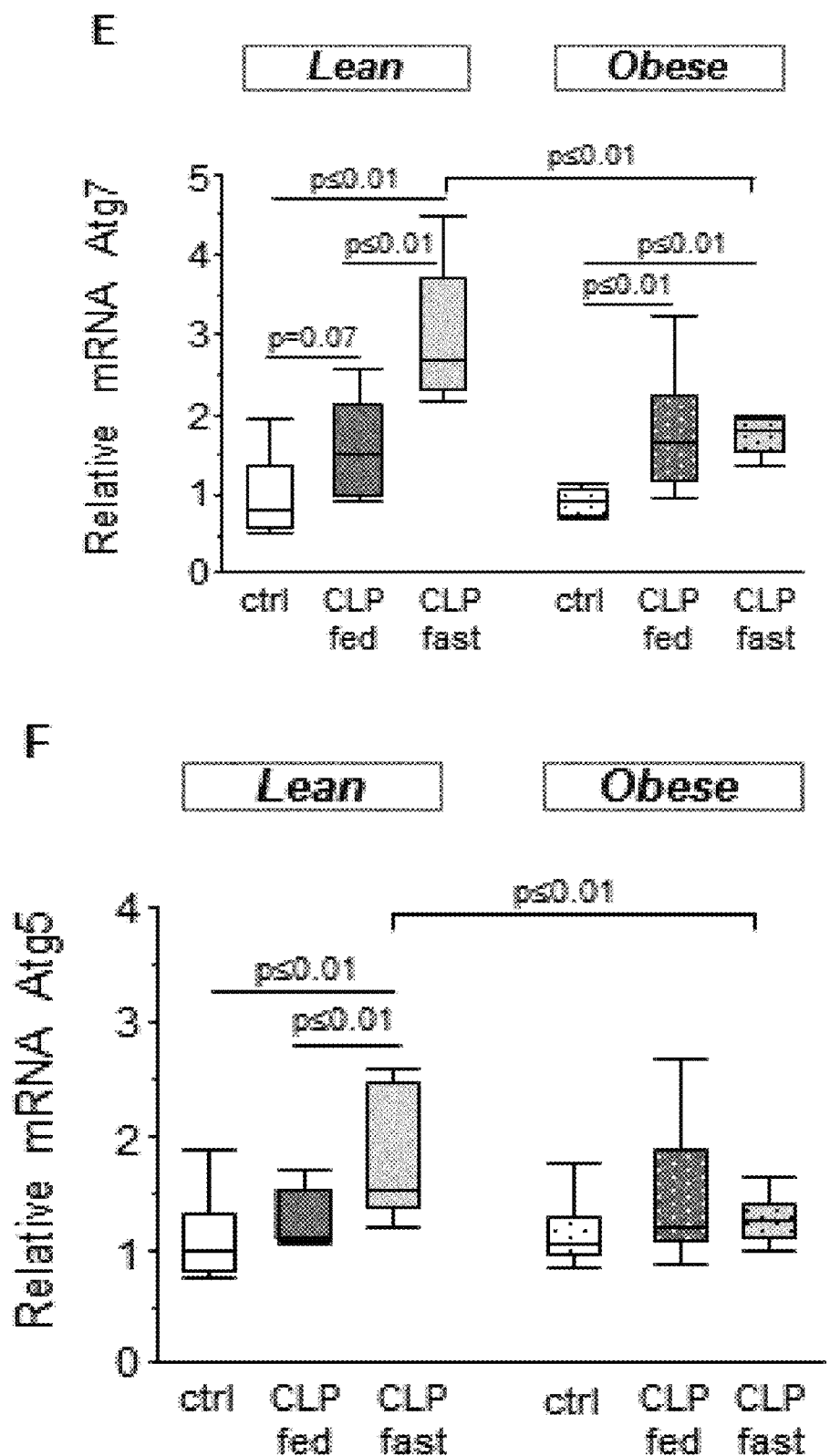
Figure 3E + 3F

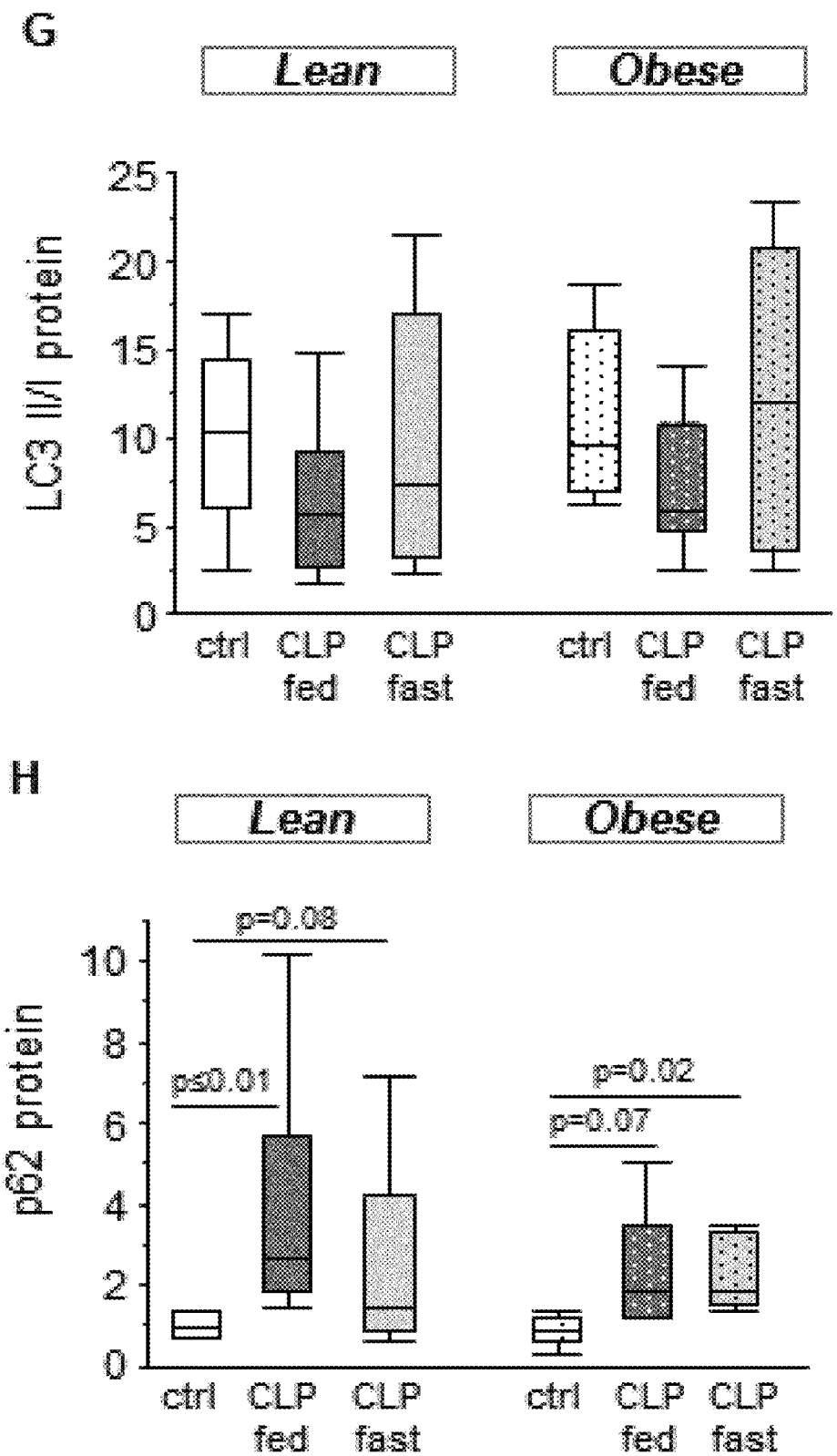
Figure 3G + 3H

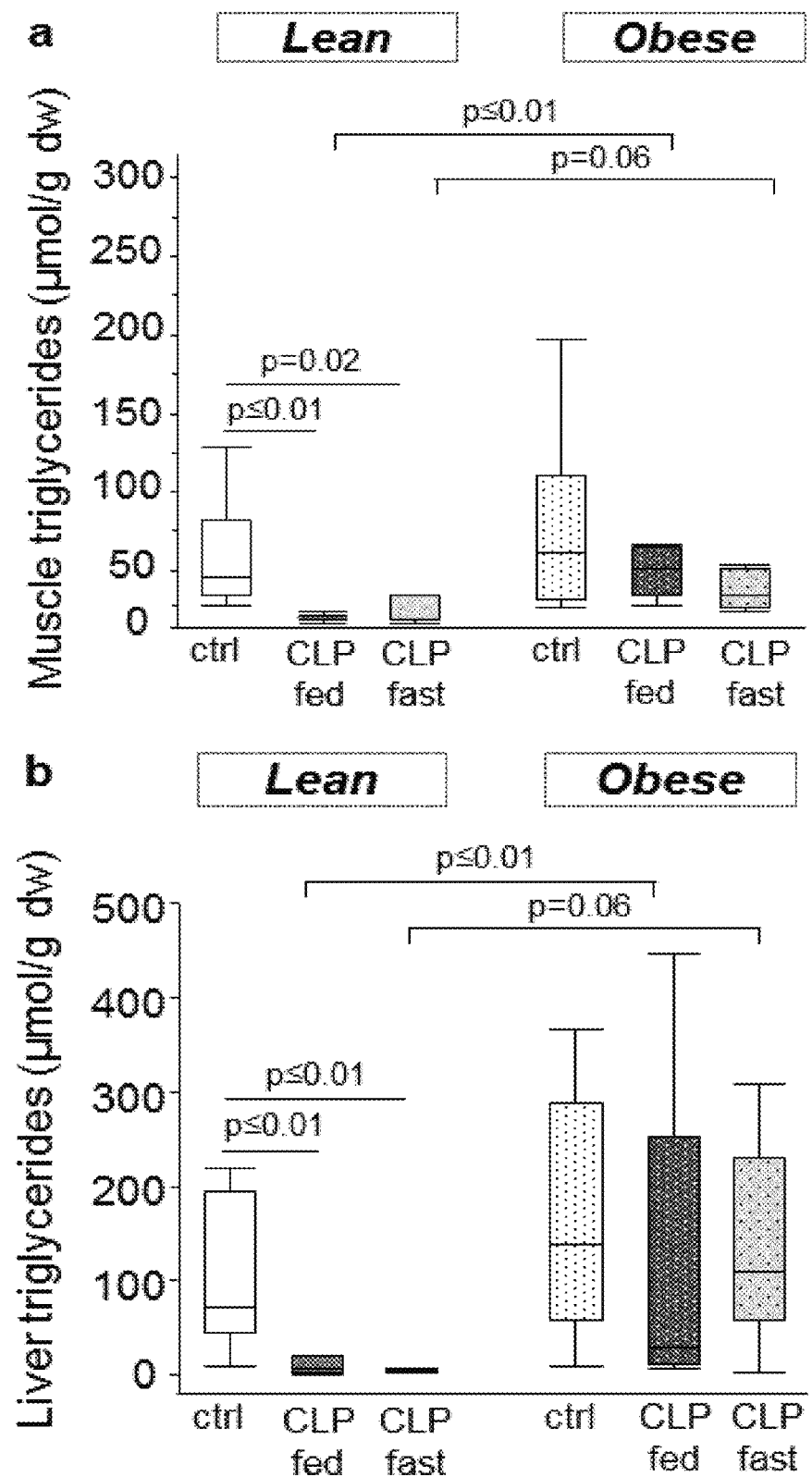
Figure 4a + 4b

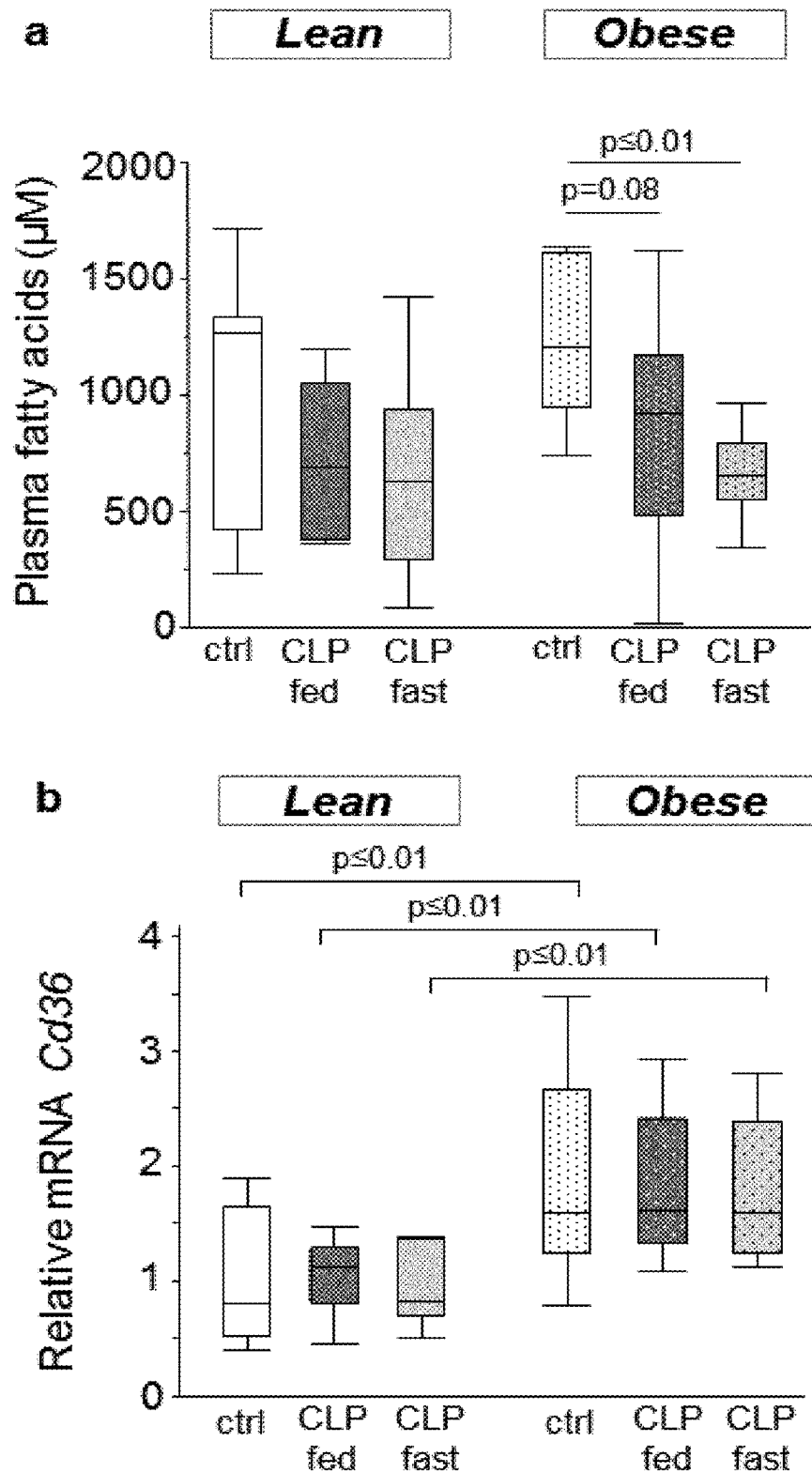
Figure 5a + 5b

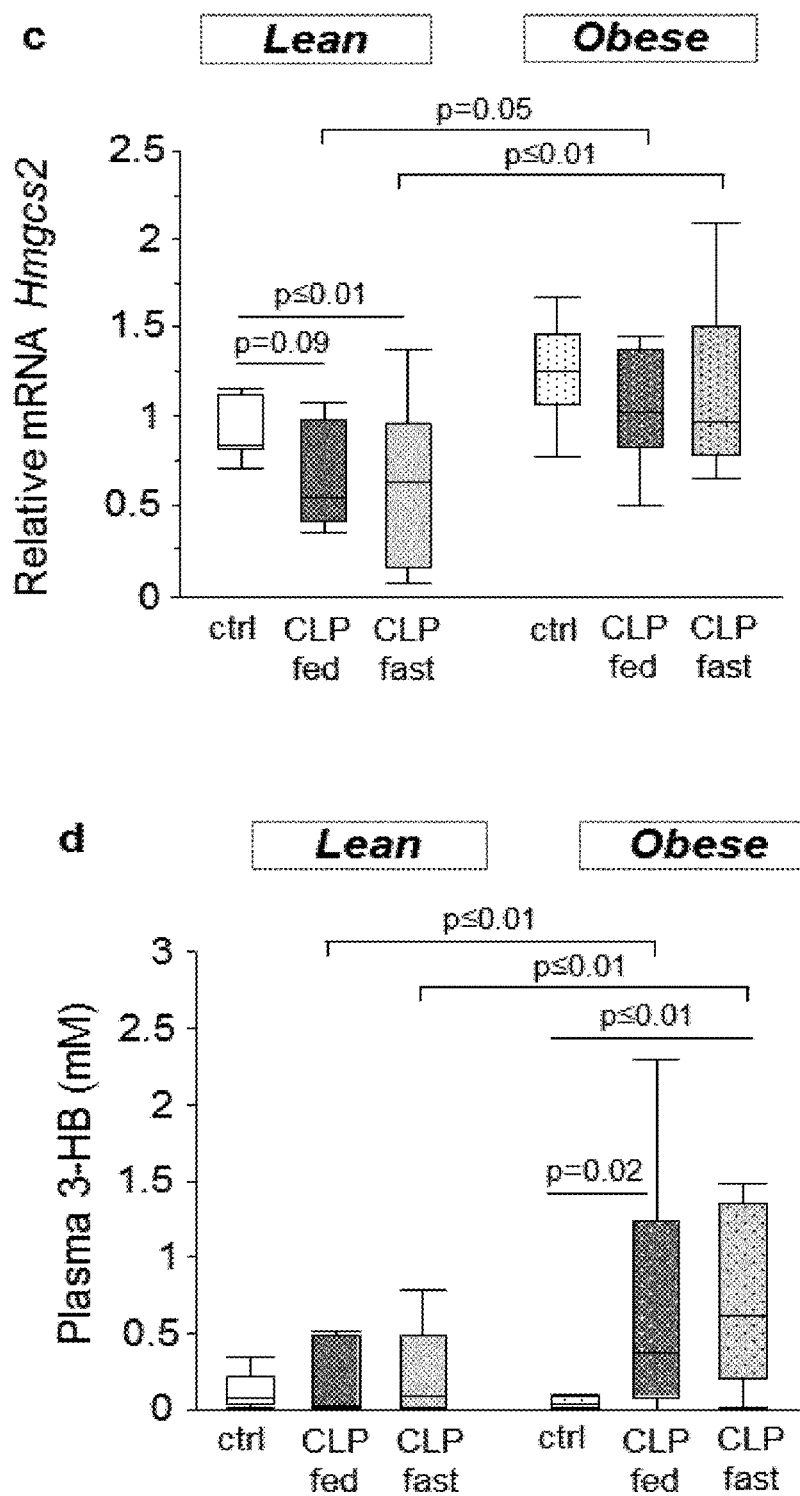
Figure 5c + 5d

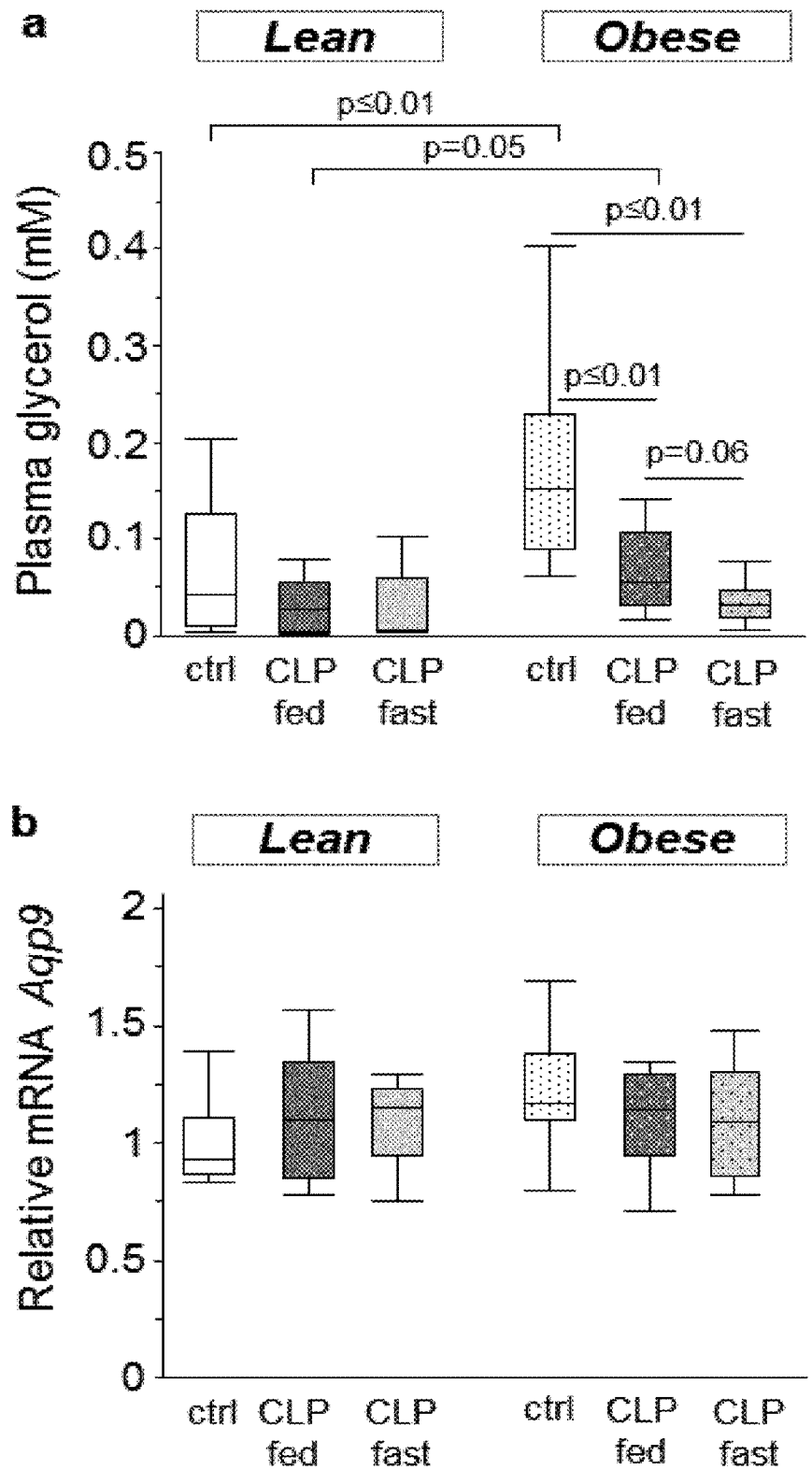
Figure 6a + 6b

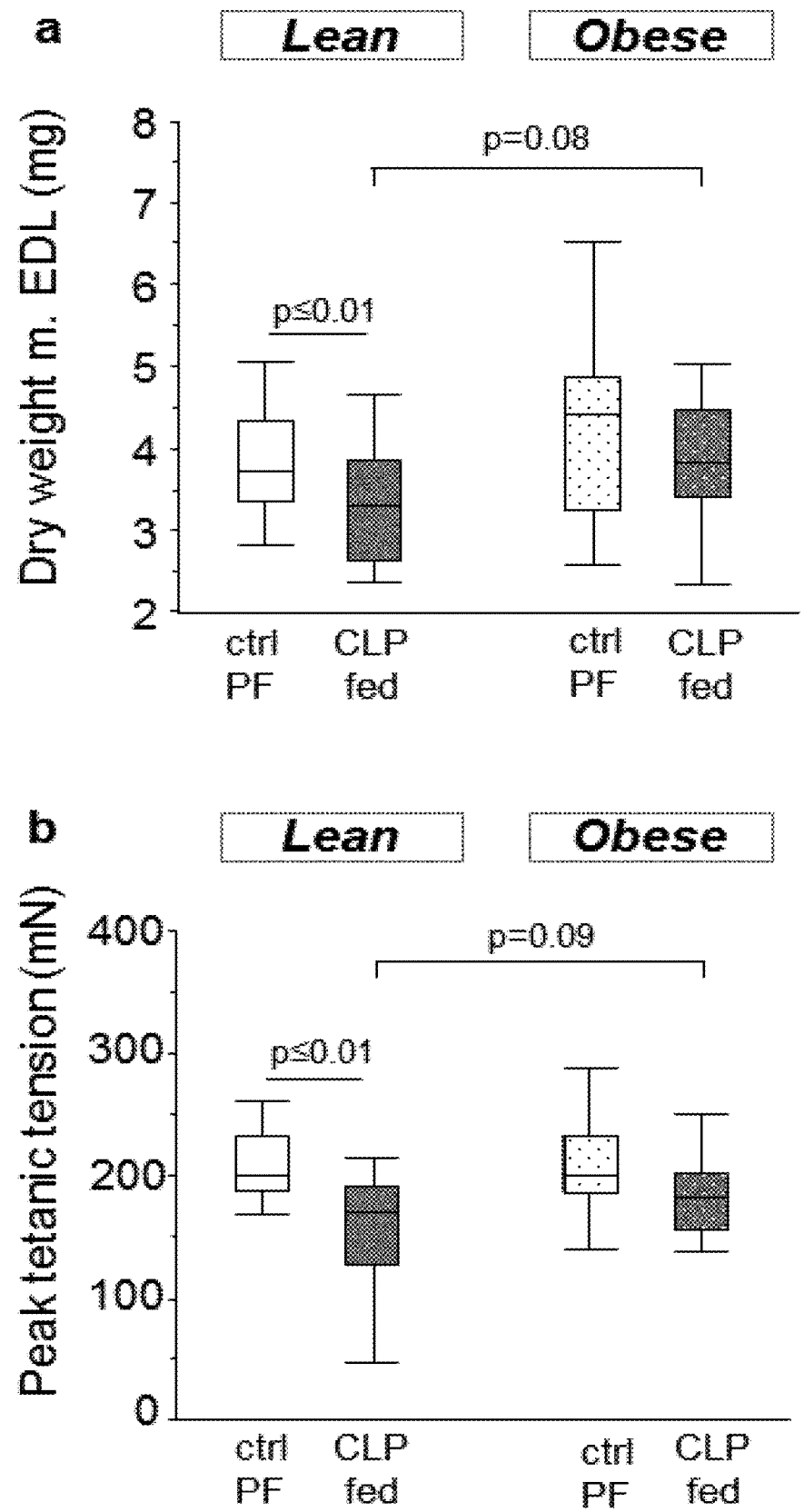
Figure 7a + 7b

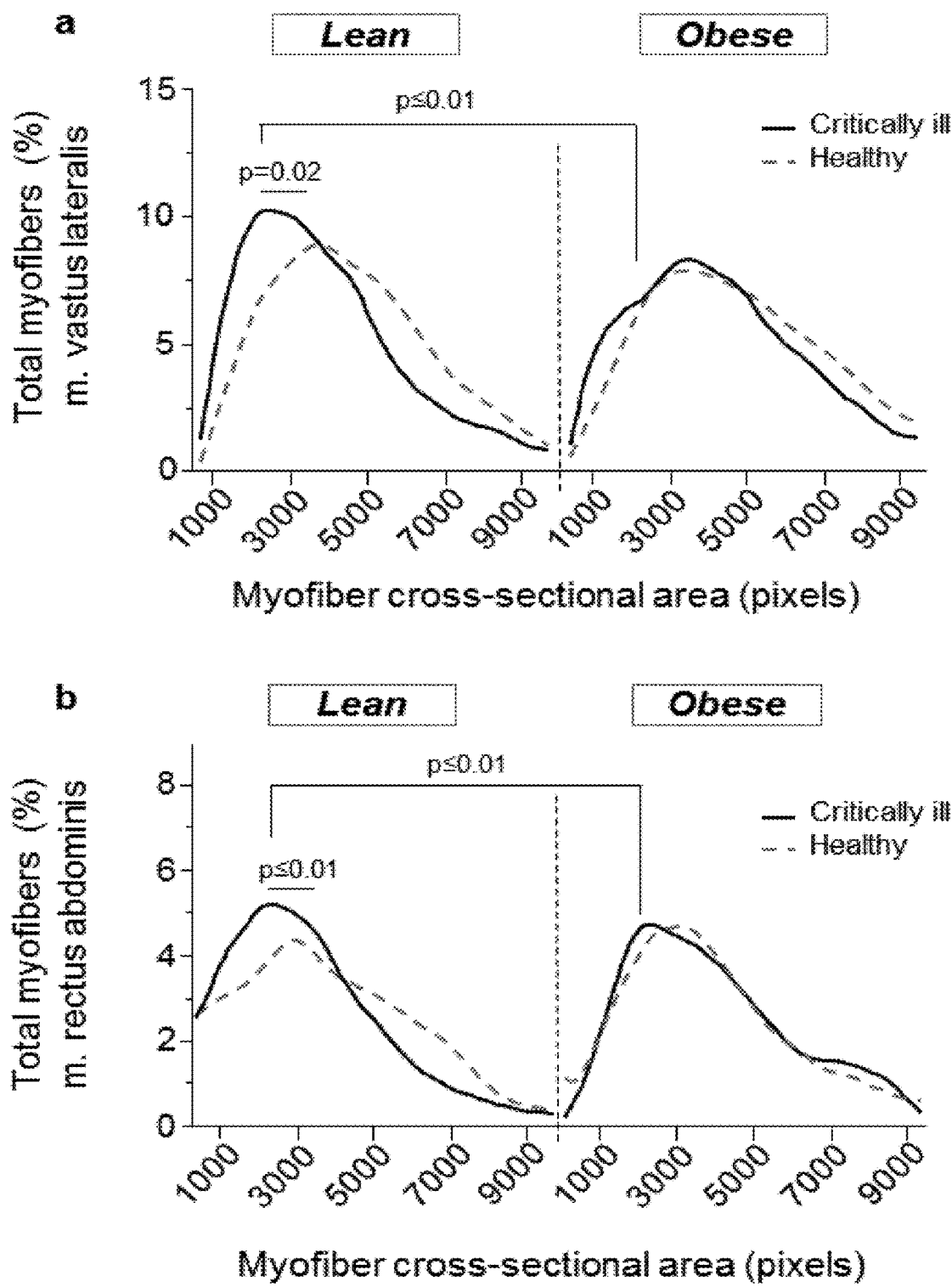
Figure 8a + 8b

Figure 11A + 11B

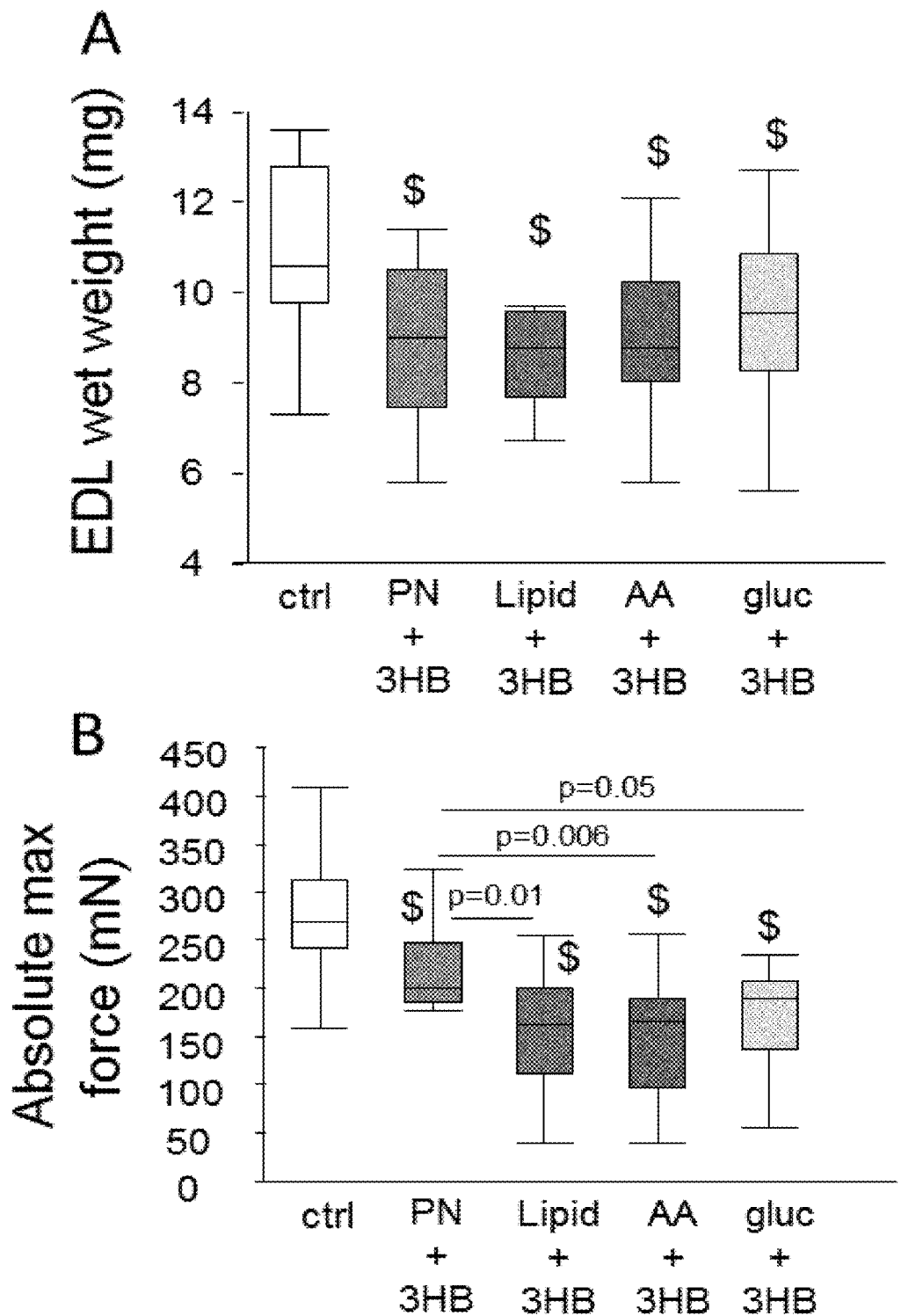
Figure 16a + 16b

3-HYDROXYBUTYRATE ALONE OR IN COMBINATION FOR USE IN THE TREATMENT OF CRITICAL CARE TREATMENT

RELATED APPLICATION

This application is a continuation of U.S. patent application Ser. No. 16/472,600, filed Jun. 21, 2019, which is a 371 application of Application No PCT/EP2017/081394, filed Dec. 4, 2017 which claimed the benefit of provisional Application No. 62/438,771, filed Dec. 23, 2016, which is herein incorporated by reference.

TECHNICAL FIELD

This invention relates generally to methods and compositions for the treatment for amelioration or prevention of sepsis, severe sepsis, severe sepsis with septic shock, critical illness myopathy and critical illness polyneuropathy and particularly to the use of a combination of parenteral or enteral feeding with a carboxylic acid.

BACKGROUND

Critical illness is defined as any acute medical condition necessitating vital organ support without which death would be imminent. Whether evoked by sepsis, severe sepsis, septic shock, trauma, major surgery, or other critical illnesses, patients can suffer from critical illness myopathy and/or critical illness polyneuropathy, a clinical manifestation referred to as intensive care unit (ICU) acquired weakness (ICUAW) (Kress J P, Hall J B 2014 NEJM 370(17): 1626-35). Prevalence of ICUAW varies according to the study population, but up to 80% of ICU patients appear to suffer from muscle wasting and/or muscle weakness. ICUAW is associated with impaired weaning from mechanical ventilation, delayed rehabilitation and prolonged hospitalization, late death and greater impaired functional outcome of survivors. Parenteral provision of macronutrients during acute critical illness does not prevent muscle weakness and may in fact exert deleterious effects via further suppression of autophagic myofiber quality control (Hermans et al, 2013 Lancet Respir Med 1(8):621-9; Derde S et al, 2012 Crit Care Med 40(1):79-89).

However, despite the major advances of the past several decades in the understanding of critical illnesses including sepsis, severe sepsis, severe sepsis with septic shock, critical illness myopathy and critical illness polyneuropathy, there is still no effective treatment to treat these conditions or reduce the symptoms such as ICUAW associated with them. There is, therefore, a need for new methods and compositions for the treatment of sepsis, severe sepsis, severe sepsis with septic shock, critical illness myopathy and critical illness polyneuropathy.

SUMMARY

It is, therefore, an object of the present invention to provide methods and compositions for treating sepsis, severe sepsis, septic shock, critical illness myopathy and critical illness polyneuropathy. It is another object of the invention to decrease the morbidity and more preferably the muscle weakness associated with sepsis, severe sepsis, septic shock, critical illness myopathy and critical illness polyneuropathy.

In accordance with another aspect of the instant invention, the above methods are used for the treatment of symptoms associated with a critical illness which includes, but is not limited to sepsis, severe sepsis, septic shock, critical illness myopathy and critical illness polyneuropathy.

This invention was based in part on the discovery that critical illness and/or sepsis, severe sepsis, septic shock, critical illness myopathy and critical illness polyneuropathy can be prevented, treated or cured, at least to a certain extent, by a composition containing a carboxylic acid, more preferably 3-hydroxybutyric acid in combination with enteral or parenteral feeding. Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

The invention relates to a method of treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) comprising administering to a subject in need thereof composition comprising 1) an 3-hydroxybutyrate, its enantiomer (R)-3-hydroxybutyric acid, (S)-3-Hydroxybutyric acid or enantiomeric mixture, or a pharmaceutically acceptable or under food law acceptable salt or a pharmaceutically acceptable or under food law acceptable ester thereof. Critical illness polyneuropathy and critical illness myopathy are overlapping syndromes of diffuse, symmetric, flaccid muscle weakness occurring in critically ill patients and involving all extremities and the diaphragm with relative sparing of the cranial nerves. An example of a for present invention suitable salt is pharmaceutically acceptable or under food law acceptable (R)-3-hydroxybutyric sodium salt or sodium (S)-3-hydroxybutyrate and an example of a for the present invention suitable ester is pharmaceutically acceptable or under food law acceptable (R)-3-hydroxybutyl (R)-3-hydroxybutyrate. Examples of a for present invention suitable administering to a subject in need thereof is a parenteral administration of a parenteral composition comprising 1) an 3-hydroxybutyrate, its enantiomer (R)-3-hydroxybutyric acid, (S)-3-Hydroxybutyric acid or enantiomeric mixture, or a pharmaceutically acceptable or under food law acceptable salt or a pharmaceutically acceptable or under food law acceptable ester thereof or enteral administration of a enteral composition comprising 1) an 3-hydroxybutyrate, its enantiomer (R)-3-hydroxybutyric acid, (S)-3-Hydroxybutyric acid or enantiomeric mixture, or a pharmaceutically acceptable or under food law acceptable salt or a pharmaceutically acceptable or under food law acceptable ester thereof. The delivery can be continuous or as bolus.

One aspect of the invention described herein relates to a method of treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) comprising administering to a subject in need thereof composition comprising 1) an 3-hydroxybutyrate, its enantiomer (R)-3-hydroxybutyric acid, (S)-3-Hydroxybutyric acid or enantiomeric mixture, or a pharmaceutically acceptable or under food law acceptable salt or a pharmaceutically acceptable or under food law acceptable ester thereof, wherein the treatment with the 3-hydroxybutyrate is carried out with a continuous or multiple dose regime at a dose range of 0.08 g/kg patient body weight to 4.13 g/kg patient body weight per 24 hours.

Another aspect of the invention described herein relates to a method of treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) comprising administering to a subject in need thereof composition comprising 1) an 3-hydroxybutyrate, its enantiomer (R)-3-hydroxybutyric acid, (S)-3-Hydroxybutyric acid or enantiomeric mixture, or a pharmaceutically acceptable or under food law acceptable salt or a pharmaceutically acceptable or under food law acceptable ester thereof, wherein the treatment with the 3-hydroxybutyrate is carried out with a continuous or multiple dose regime at a dose range of 0.8 mmol/kg patient body weight to 39.7 mmol/kg patient body weight per 24 hours.

Yet another aspect of the invention described herein relates to a method of treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) comprising administering to a subject in need thereof composition comprising 1) an 3-hydroxybutyrate, its enantiomer (R)-3-hydroxybutyric acid, (S)-3-Hydroxybutyric acid or enantiomeric mixture, or a pharmaceutically acceptable or under food law acceptable salt or a pharmaceutically acceptable or under food law acceptable ester thereof, wherein the treatment with the 3-hydroxybutyrate is carried out with a continuous or bolus, parenteral or enteral dose range of 0.08 g/kg to 4.13 g/kg patient body weight per 24 hours. In some embodiments this treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) is carried out with 3-hydroxybutyrate as a continuous or bolus, parenteral or enteral dose range of 0.8 mmol/kg patient body weight to 39.7 mmol/kg patient body weight per 24 hours. In some other embodiment this treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) is carried out with 3-hydroxybutyrate that is administered to a patient at a daily dose of about 1.6 mmol/kg to 79.3 mmol/kg, preferably of about 1.6 mmol/kg to 31.7 mmol/kg, more preferably of about 3.2 mmol/kg.

Applicant has discovered that the particular compositions described herein provide unexpectedly high muscle force improvement and effectively overcome critical illness myopathy or neuromyopathy or critical illness polyneuropathy in combinational therapy formulated together and in individual dosage amounts or formulated separately and in individual dosage amounts with a chemical energy providing macronutrient or caloric organic compound comprising at least one macronutrient member of one of the macronutrient groups 1) a macronutrient group consisting of amino acid, peptide and protein or combination thereof and 2) a macronutrient group consisting of fatty acid, glycerol, glyceride and triglyceride or combination thereof and 3) a macronutrient group consisting of monosaccharide, disaccharide, oligosaccharide and polysaccharide or combination thereof. One object of the invention described herein thus concerns a method for treating such for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) comprising administering to a subject in need thereof such composition comprising an 3-hydroxybutyrate, wherein the 3-hydroxybutyrate is in combinational therapy formulated together and in individual dosage amounts or formulated separately and in individual dosage amounts with a chemical energy providing macronutrient or caloric organic compound comprising at least one macronutrient member of one of the macronutrient groups 1) a macronutrient group consisting of amino acid, peptide and protein or combination thereof and 2) a macronutrient group consisting of fatty acid, glycerol, glyceride and triglyceride or combination thereof and 3) a macronutrient group consisting of monosaccharide, disaccharide, oligosaccharide and polysaccharide or combination thereof. Another object of the invention described herein thus concerns a method for treating such for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) comprising administering to a subject in need thereof such composition comprising an 3-hydroxybutyrate, wherein the 3-hydroxybutyrate is in combinational therapy formulated together and in individual dosage amounts or formulated separately and in individual dosage amounts with a chemical energy providing macronutrient or caloric organic compound comprising at least one macronutrient member of two macronutrient groups each of the macronutrient groups 1) a macronutrient group consisting of amino acid, peptide and protein or combination thereof and 2) a macronutrient group consisting of fatty acid, glycerol, glyceride and triglyceride or combination thereof and 3) a macronutrient group consisting of monosaccharide, disaccharide, oligosaccharide and polysaccharide or combination thereof. Yet another object of the invention described herein thus concerns a method for treating such for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) comprising administering to a subject in need thereof such composition comprising an 3-hydroxybutyrate, wherein the 3-hydroxybutyrate is in combinational therapy formulated together and in individual dosage amounts or formulated separately and in individual dosage amounts with a chemical energy providing macronutrient or caloric organic compound comprising at least one macronutrient member of each of the three macronutrient groups 1) a macronutrient group consisting of amino acid, peptide and protein or combination thereof and 2) a macronutrient group consisting of fatty acid, glycerol, glyceride and triglyceride or combination thereof and 3) a macronutrient group consisting of monosaccharide, disaccharide, oligosaccharide and polysaccharide or combination thereof.

The present therapies have been shown to be highly effective in critical illness of lean subjects. A certain aspect of the invention described herein thus concerns a method for treating such for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) comprising administering to a subject in need thereof such composition comprising an 3-hydroxybutyrate, wherein the patient has a BMI under 24.9, wherein the patient is a normal weight patient with a BMI between 18.5 and 24.9 or wherein the patient is an underweight patient with a BMI under 18.5.

The composition of treatment of present invention can further comprising one or more pharmaceutically acceptable or under food law acceptable adjuvants, carriers, excipients, and/or diluents.

The present disclosure relates in an aspect also to a 3-hydroxybutyrate of the groups consisting of an 3-hydroxybutyrate, its enantiomer (R)-3-hydroxybutyric acid, (S)-3-Hydroxybutyric acid or enantiomeric mixture, or a pharmaceutically acceptable or under food law acceptable salt or a pharmaceutically acceptable or under food law acceptable ester thereof for use in a treatment to prevent or ameliorate critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) in a subject in need thereof. In a certain embodiment these pharmaceutically acceptable or under food law acceptable salts are (R)-3-hydroxybutyric sodium salt or sodium (S)-3-hydroxybutyrate. In yet another embodiment the pharmaceutically acceptable or under food law acceptable ester is (R)-3-hydroxybutyl (R)-3-hydroxybutyrate. A particular aspect of present invention is that the 3-hydroxybutyrate for use in a treatment to prevent or ameliorate critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) in a subject in need thereof, whereby the treatment with the 3-hydroxybutyrate is carried out with a continuous or multiple dose regime at a dose range of 0.08 g/kg patient body weight to 4.13 g/kg patient body weight per 24 hours. Another particular aspect of present invention is that the 3-hydroxybutyrate for use in a treatment to prevent or ameliorate critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) in a subject in need thereof, wherein the treatment with the 3-hydroxybutyrate is carried out with a continuous or multiple dose regime at a dose range of 0.8 mmol/kg patient body weight to 39.7 mmol/kg patient body weight per 24 hours. Yet another particular aspect of present invention is that the 3-hydroxybutyrate for use in a treatment to prevent or ameliorate critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) in a subject in need thereof, wherein the treatment with the 3-hydroxybutyrate is carried out with a continuous or bolus, parenteral or enteral dose range of 0.08 g/kg to 4.13 g/kg patient body weight per 24 hours.

Yet another particular aspect of present invention is that the 3-hydroxybutyrate for use in a treatment to prevent or ameliorate critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) in a subject in need thereof, wherein the treatment with the 3-hydroxybutyrate is carried out with a continuous or bolus, parenteral or enteral dose range of 0.8 mmol/kg patient body weight to 39.7 mmol/kg patient body weight per 24 hours. Yet another particular aspect of present invention is that the 3-hydroxybutyrate for use in a treatment to prevent or ameliorate critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) in a subject in need thereof, wherein the 3-hydroxybutyrate is administered to a patient at a daily dose of about 1.6 mmol/kg to 79.3 mmol/kg, preferably of about 1.6 mmol/kg to 31.7 mmol/kg, more preferably of about 3.2 mmol/kg.

The applicants found that the treatment with the 3-hydroxybutyrate is drastically efficient in the critical ill subjects which also receive chemical energy providing macronutrient or caloric organic compounds.

Yet another aspect of present invention is the 3-hydroxybutyrate of present invention for use treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM), wherein the 3-hydroxybutyrate is in combinational therapy formulated together and in individual dosage amounts or formulated separately and in individual dosage amounts with a chemical energy providing macronutrient or caloric organic compound comprising at least one macronutrient member of one of the three macronutrient groups or of two of the three macronutrient groups each or of each of the three macronutrient groups 1) a macronutrient group consisting of amino acid, peptide and protein or combination thereof and 2) a macronutrient group consisting of fatty acid, glycerol, glyceride and triglyceride or combination thereof and 3) a macronutrient group consisting of monosaccharide, disaccharide, oligosaccharide and polysaccharide or combination thereof.

A lean critically ill subject was found to be in high need for the 3-hydroxybutyrate treatment of present invention and the present therapies have been shown to be highly effective in critical ill lean subjects. It is thus an object of present invention to use to provide a 3-hydroxybutyrate for use treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM), wherein the patient has a BMI under 24.9. Another object of present invention is to provide a 3-hydroxybutyrate for use treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM), wherein the patient is a normal weight patient with a BMI between 18.5 and 24.9. Yet another aspect of present invention is to provide a 3-hydroxybutyrate for use treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM), wherein the patient is an underweight patient with a BMI under 18.5. This 3-hydroxybutyrate of the composition comprising 3-hydroxybutyrate for use according to present invention, can further comprise one or more pharmaceutically acceptable or under food law acceptable adjuvants, carriers, excipients, and/or diluents.

The present disclosure relates in another aspect also to a pack or a composition for use in a combinational therapy of treating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM), the pack or composition comprising an 3-hydroxybutyrate, its enantiomer (R)-3-hydroxybutyric acid, (S)-3-Hydroxybutyric acid or enantiomeric mixture, or a pharmaceutically or under food law acceptable salt, for instance (R)-3-hydroxybutyric sodium salt or sodium (S)-3-hydroxybutyrate, or a pharmaceutically acceptable or under food law acceptable ester thereof, for instance (R)-3-hydroxybutyl (R)-3-hydroxybutyrate and a macronutrient mixture comprising at least one macronutrient member of one of the three macronutrient groups or of two of the three macronutrient groups each or of each of the three macronutrient groups 1) a macronutrient group consisting of amino acid, peptide and protein or combination thereof and 2) a macronutrient group consisting of fatty acid, glycerol, glyceride and triglyceride or combination thereof and 3) a macronutrient group consisting of monosaccharide, disaccharide, oligosaccharide and polysaccharide or combination thereof. This pack may be for use in a combinational therapy of treating or preventing of a disorder of c critical illness myopathy (2016/17 ICD-10-CM Diagnosis Code G72.81), critical illness polyneuropathy (2016/17 ICD-10-CM Diagnosis Code G62.81) or critical illness neuromyopathy (CINM), whereby the disorder is evoked, induced or enhanced by disorder of the group consisting of sepsis (2016/17 ICD-10-CM Diagnosis Code A41.9), severe sepsis (2016/17 ICD-10-CM Diagnosis Code R65.2), severe sepsis with septic shock (2016/2017 ICD-10-CM Diagnosis Code R.65.21) or it may be for use in a combinational treatment to prevent or ameliorate muscle weakness (2017 ICD-10-CM Diagnosis Code M62.81) evoked, induced or enhanced by a critical illness myopathy 2016/17 (ICD-10-CM Diagnosis Code G72.81) or critical illness neuromyopathy (2016/17 ICD-10-CM Diagnosis Code G62.81) disorder.

Such pack or composition of present invention for use for use in a combinational therapy of treating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM), can comprise the 3-hydroxybutyrate and said macronutrient mixture formulated together and in individual dosage amounts.

In a particular aspect the pack or composition for use in a combinational therapy of treating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM), is so designed that the treatment with 3-hydroxybutyrate can be carried out with a continuous or multiple dose regime at a dose range of 0.08 g/kg patient body weight to 4.13 g/kg patient body weight per 24 hours.

In yet another a particular aspect the pack or composition for use in a combinational therapy of treating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM), is so designed that the treatment with 3-hydroxybutyrate can be carried out with a continuous or multiple dose regime at a dose range of 0.8 mmol/kg patient body weight to 39.7 mmol/kg patient body weight per 24 hours.

In yet another a particular aspect the pack or composition for use in a combinational therapy of treating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM), is so designed that the treatment with 3-hydroxybutyrate can be carried out with a continuous or bolus, parenteral or enteral dose range of 0.08 g/kg to 4.13 g/kg patient body weight per 24 hours.

In yet another a particular aspect the pack or composition for use in a combinational therapy of treating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM), is so designed that the treatment with 3-hydroxybutyrate can be carried out with a continuous or bolus, parenteral or enteral dose range of 0.8 mmol/kg patient body weight to 39.7 mmol/kg patient body weight per 24 hours.

The present invention provides also a pack or composition for use of treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) whereby the pack comprises an 3-hydroxybutyrate, its enantiomer (R)-3-hydroxybutyric acid, (S)-3-Hydroxybutyric acid or enantiomeric mixture, or a pharmaceutically acceptable or under food law acceptable salt or a pharmaceutically acceptable or under food law acceptable ester thereof and wherein is designed for 3-hydroxybutyrate administration to a patient at a daily dose of about 1.6 mmol/kg to 79.3 mmol/kg, preferably of about 1.6 mmol/kg to 31.7 mmol/kg, more preferably of about 3.2 mmol/kg.

The present invention provides also a pack or composition for use of treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) whereby the pack comprises an 3-hydroxybutyrate, its enantiomer (R)-3-hydroxybutyric acid, (S)-3-Hydroxybutyric acid or enantiomeric mixture, or a pharmaceutically acceptable or under food law acceptable salt or a pharmaceutically acceptable or under food law acceptable ester thereof, wherein the 3-hydroxybutyrate is present in said composition in an amount equivalent to 1-70 grams.

The present invention provides also a pack or composition for use of treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) whereby the pack comprises an 3-hydroxybutyrate, its enantiomer (R)-3-hydroxybutyric acid, (S)-3-Hydroxybutyric acid or enantiomeric mixture, or a pharmaceutically acceptable or under food law acceptable salt or a pharmaceutically acceptable or under food law acceptable ester thereof, wherein the 3-hydroxybutyrate is present in said composition in an amount equivalent to 5-60 grams.

The present invention provides also a pack or composition for use of treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) whereby the pack comprises an 3-hydroxybutyrate, its enantiomer (R)-3-hydroxybutyric acid, (S)-3-Hydroxybutyric acid or enantiomeric mixture, or a pharmaceutically acceptable or under food law acceptable salt or a pharmaceutically acceptable or under food law acceptable ester thereof, wherein the 3-hydroxybutyrate is present in said composition in an amount equivalent to 10-50 grams.

The present invention provides also a pack or composition for use of treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) whereby the pack comprises an 3-hydroxybutyrate, its enantiomer (R)-3-hydroxybutyric acid, (S)-3-Hydroxybutyric acid or enantiomeric mixture, or a pharmaceutically acceptable or under food law acceptable salt or a pharmaceutically acceptable or under food law acceptable ester thereof, wherein the 3-hydroxybutyrate is present in said composition in an amount equivalent to 0.05-10 grams.

The present invention provides also a pack or composition for use of treatment for ameliorating or preventing of critical illness myopathy (2016/17 ICD-10-CM Diagnosis Code G72.81), critical illness polyneuropathy (2016/17 ICD-10-CM Diagnosis Code G62.81) or critical illness neuromyopathy (CINM) whereby the pack comprises an 3-hydroxybutyrate, its enantiomer (R)-3-hydroxybutyric acid, (S)-3-Hydroxybutyric acid or enantiomeric mixture, or a pharmaceutically acceptable or under food law acceptable salt or a pharmaceutically acceptable or under food law acceptable ester thereof, wherein the 3-hydroxybutyrate is present in said composition in an amount equivalent to 0.08-4.13 grams. In a particular aspect said composition is formulated for systemic administration.

In yet another embodiment of the invention, the composition is used without causing or without aggravating a hepato-pancreato-biliary disorder. In a more particular embodiment the composition is used without causing or without aggravating fatty liver or without aggravating or causing nonalcoholic steatohepatitis (NASH) (2017 ICD-10-CM Diagnosis Code K75.81).

DESCRIPTION OF THE DRAWINGS

The present invention will become more fully understood from the detailed description given herein below and the accompanying drawings which are given by way of illustration only, and thus are not limitative of the present invention, and wherein:

FIG. 1 Mice body composition. (a) Body weight after 5 days of CLP-induced critical illness (ANOVA p≤0.01). (b) Loss of body weight during the 5-day experiment (ANOVA p=0.4). (c) End body fat mass, measured by DEXA (ANOVA p≤0.01). (d) Loss in body fat mass during 5 days of critical illness (ANOVA p≤0.01). White, healthy lean mice (n=8); dark gray, fed lean CLP mice (n=7); light gray, fasted lean CLP mice (n=9); white dotted, healthy obese mice (n=9); dark gray dotted, fed obese CLP mice (n=10); light gray dotted, fasted obese CLP mice (n=9). [DEXA: dual-energy-X-ray-absorptiometry, CLP: cecal ligation and puncture, ctrl: healthy control animals, fed: parenterally fed, fast: fasted]

FIG. 3 Mice skeletal muscle atrophy and autophagy. (a) Relative mRNA expression of Fbxo32 (ANOVA p≤0.01). (b) Relative mRNA expression of Trim63 (ANOVA p≤0.01). (c) Activity of the 20S-proteasome (ANOVA p=0.9). (d) Cathepsin activity (ANOVA p=0.4). (e) Relative mRNA expression of Atg7 (ANOVA p≤0.01). (f) Relative mRNA expression of Atg5 (ANOVA p≤0.01). (g) LC3-II/LC3-1 protein ratio, as detected with western blot (ANOVA p=0.4). (h) Protein level of p62, measured with western blot (ANOVA p≤0.01). Gene expression data are expressed normalized to Rn18s gene expression and as a fold change of the mean of the lean healthy controls. Protein levels are presented as fold change of the mean of lean healthy controls. White, healthy lean mice (n=8); dark gray, fed lean CLP mice (n=7); light gray, fasted lean CLP mice (n=9); white dotted, healthy obese mice (n=9); dark gray dotted, fed obese CLP mice (n=10); light gray dotted, fasted obese CLP mice (n=9). [dw: dry weight, CLP: cecal ligation and puncture, ctrl: healthy control animals, fed: parenterally fed, fast: fasted]

FIG. 4 Mice muscle and hepatic triglyceride content. (a) Triglyceride content of skeletal muscle tissue (Mann-Whitney p≤0.01). (b) Hepatic triglyceride content (Mann-Whitney p≤0.01). White, healthy lean mice (n=8); dark gray, fed lean CLP mice (n=7); light gray, fasted lean CLP mice (n=9); white dotted, healthy obese mice (n=9); dark gray dotted, fed obese CLP mice (n=10); light gray dotted, fasted obese CLP mice (n=9). [dw: dry weight, CLP: cecal ligation and puncture, ctrl: healthy control animals, fed: parenterally fed, fast: fasted]

FIG. 5 Mice fatty acid metabolism. (a) Serum fatty acid concentration (ANOVA p≤0.01). (b) Relative mRNA expression of Cd36 (ANOVA p≤0.01). (c) Relative Hmgcs2 mRNA expression (ANOVA p≤0.01). (d) Ketone body serum concentration (ANOVA p<0.01). Gene expression data are expressed normalized to Rn18s gene expression and as a fold change of the mean of the lean healthy controls. White, healthy lean mice (n=8); dark gray, fed lean CLP mice (n=7); light gray, fasted lean CLP mice (n=9); white dotted, healthy obese mice (n=9); dark gray dotted, fed obese CLP mice (n=10); light gray dotted, fasted obese CLP mice (n=9). [CLP: cecal ligation and puncture, ctrl: healthy control animals, fed: parenterally fed, fast: fasted, 3-HB: 3-hydroxybutyric acid]

FIG. 8 Muscle cross-sectional area in prolonged critically ill patients. (a) m. vastus lateralis myofiber cross-sectional area of in vivo biopsies from lean (BMI≤525; n=51) and overweight/obese (BMI>25; n=51) prolonged critically ill patients and lean (n=11) and overweight/obese (n=9) healthy controls. (b) m. rectus abdominis myofiber cross-sectional area of postmortem biopsies from lean (n=43) and overweight/obese (n=43) prolonged critically ill patients and lean (n=4) and overweight/obese (n=7) healthy controls. Cross-sectional area is categorized in blocks of 1000 pixels. The graph displays smoothed curves of the percentage myofibers in each category, split up for critically ill patients (black line) and healthy controls (gray dotted line). Statistical difference reflects a change in proportion of small (<2000) myofibers.

DETAILED DESCRIPTION

Definitions

Figure 2C:
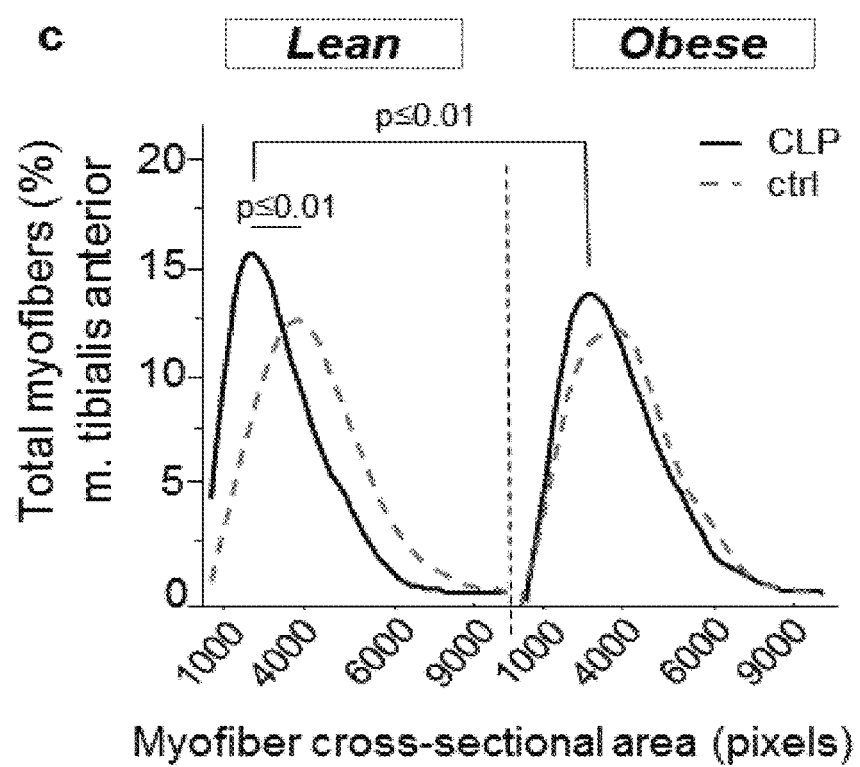
FIG. 2 Mice skeletal muscle mass and cross-sectional area. (a) Dry weight of the m. tibialis anterior (ANOVA p≤0.01). (b) Dry weight of the m. soleus (ANOVA p≤0.01). White, healthy lean mice (n=8); dark gray, fed lean CLP mice (n=7); light gray, fasted lean CLP mice (n=9); white dotted, healthy obese mice (n=9); dark gray dotted, fed obese CLP mice (n=10); light gray dotted, fasted obese CLP mice (n=9). (c) Skeletal muscle myofiber cross-sectional area (ANOVA p≤0.01). Cross-sectional area is categorized in blocks of 1000 pixels for each animal. The graph displays smoothed curves of the percentage of myofibers in each category, gray dotted line, healthy animals; black line, CLP mice. Statistical difference reflects mean myofiber cross-sectional area. Fed and fasted CLP mice were grouped as they were similar (p=0.3 in lean CLP; p=0.4 in obese CLP). [CLP: cecal ligation and puncture, ctrl: healthy control animals, fed: parenterally fed, fast: fasted]

In describing the present invention, the following terms will be employed, and are intended to be defined as indicated below.

The caloric target in the meaning of this application is a caloric target calculated as the caloric need times the Corrected Ideal Body Weight. The formula for calculating Ideal Body Weight for a female patient is 45.5+[0.91×(height in cm−152.4)] and for a male patient 50+[0.91×(height in cm−152.4)]. If BMI<18.5, the Corrected Ideal Body Weight is (Ideal Body Weight+Actual Body Weight)/2, if 27≥BMI≥18.5, the Corrected Ideal Body Weight is the Ideal Body Weight, if BMI>27, the Corrected Ideal Body Weight is the Ideal Body Weight×1.2. The caloric need for a female patient>60 years is 24 kcal/kg/day, the caloric need for a male patient>60 years is 30 kcal/kg/day, the caloric need for a female patient≤60 years is 30 kcal/kg/day, the caloric need for a male patient≤60 years it is 36 kcal/kg/day.

It must be noted that the caloric calories required for pediatric ICU patients differ from adults, for instance caloric calories required for pediatric ICU patients is 100 Cal/kg/day for a body weight 0-10 kg, 1000+(50/kg over 10 kg) for a body weight of 10-20 kg, and 1500+(20/kg over 20 kg) for a body weight>20 kg. It has to be understood that likewise the claimed ratio chemical energy providing macronutrient or caloric organic compounds in the medical compositions are adaptable for pediatric ICU patients.

It must be noted that, as used in this specification and the appended claims, the singular forms "a," "an" and "the" include plural referents unless the content clearly dictates otherwise.

The term "about," particularly in reference to a given quantity, is meant to encompass deviations of plus or minus five percent.

The terms "subject," "individual," and "patient," are used interchangeably herein and refer to any animal, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like, and transgenic animals. In some cases, the methods of the invention find use in experimental animals, in veterinary applications, and in the development of animal models for disease. Preferably, the patient is a human.

The term "parenterally" or "parenteral administration" as used herein means administration of a product by means of injection, such as injection into a vein (intravenous administration), into a muscle (intramuscular administration), under the skin (subcutaneous administration) or intraperitoneal injection.

The term "enterally" or "enteral administration" as used herein refers to the introduction of a product into the stomach or intestines, such as by tube feeding or by peroral administration (such as eating). In particular enteral administration refers to the introduction of a product into the stomach or intestines via a tube.

The term "Sepsis" has been described under 2016/17 ICD-10-CM Diagnosis Code A41.9 in the ICD-10-CM Diagnosis Codes and means the presence of a bacteria or their toxins in the blood or tissues.

The term "Severe sepsis" has been described under 2016/17 ICD-10-CM Diagnosis Code R65.2 in the ICD-10-CM Diagnosis Codes and means sepsis associated with organ dysfunction distant from the site of infection.

The term "Severe sepsis with septic shock" has been described under 2016/2017 ICD-10-CM Diagnosis Code R.65.21 and means life-threatening low blood pressure (shock) due to sepsis The term "Critical illness myopathy" has been described under 2016/17 ICD-10-CM Diagnosis Code G72.81 in the ICD-10-CM Diagnosis Codes. The term "Critical illness polyneuropathy" has been described under 2016/17 ICD-10-CM Diagnosis Code G62.81 in the ICD-10-CM Diagnosis Codes. Both Critical illness myopathy and Critical illness polyneuropathy refers to a syndrome of diffuse, symmetric, flaccid muscle weakness occurring in critically ill patients and involving all extremities and the diaphragm with relative sparing of the cranial nerves. Critical illness myopathy and Critical illness polyneuropathy have similar symptoms and presentations and are often distinguished largely on the basis of specialized electrophysiological testing or muscle and nerve biopsy.

In its broadest sense, the term a "critically ill patient", as used herein refers to a patient who has sustained or are at risk of sustaining acutely life-threatening single or multiple organ system failure due to disease or injury, a patient who is being operated and where complications supervene, and a patient who has been operated in a vital organ within the last week or has been subject to major surgery within the last week. In a more restricted sense, the term a "critically ill patient", as used herein refers to a patient who has sustained or are at risk of sustaining acutely life-threatening single or multiple organ system failure due to disease or injury, or a patient who is being operated and where complications supervene. In an even more restricted sense, the term a "critically ill patient", as used herein refers to a patient who has sustained or are at risk of sustaining acutely life-threatening single or multiple organ system failure due to disease or injury. Similarly, these definitions apply to similar expressions such as "critical illness in a patient" and a "patient is critically ill".

The term "Intensive Care Unit" (herein designated ICU), as used herein refers to the part of a hospital where critically ill patients are treated. Of course, this might vary from country to country and even from hospital to hospital and said part of the hospital may not necessary, officially, bear the name "Intensive Care Unit" or a translation or derivation thereof. Of course, the term "Intensive Care Unit" also covers a nursing home, a clinic, for example, a private clinic, or the like if the same or similar activities are performed there.

The term "lipid" refers to a fat or fat-like substance that is insoluble in polar solvents such as water. The term "lipid" is intended to include true fats (e.g. esters of fatty acids and glycerol); lipids (phospholipids, cerebrosides, waxes); sterols (cholesterol, ergosterol) and lipoproteins (e.g. HDL, LDL and VLDL).

The term "BMI" or "body mass index" refers to the ratio of weight (kg)/height (m2) and can be used to define whether a subject is underweight, normal, overweight, obese or severely obese. Typically, according to WHO criteria, a subject is underweight if he has a BMI<18.5; normal if he has a BMI of 18.5-24.9, overweight if he has a BMI of 25-29.9, class I obese if he has a BMI of 30-34.9, class II obese if he has a BMI of 35-39.9 and class III or severely obese if he has a BMI>40.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) increasing survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease, (f) improving the condition of the patient (e.g., in one or more symptoms), etc.

The term "administration" as used herein refers to delivery of at least one therapeutic agent to a patient.

"Pharmaceutically acceptable or under food law acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable or under food law acceptable cations include, but are not limited to, sodium, potassium, calcium, aluminum, lithium, and ammonium (including substituted ammonium).

The term "pharmaceutically acceptable or under food law acceptable ester" as used herein, either alone or in combination with another substituent, means esters of the carboxylic acid in which any of the carboxyl functions of the molecule, is replaced by an alkoxycarbonyl function: in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, C1-4 alkyl or C1-4 alkoxy. Other suitable prodrug esters can be found in Design of prodrugs, Bundgaard, H. Ed. Elsevier (1985) incorporated herewith by reference. Such pharmaceutically acceptable or under food law acceptable esters are usually hydrolyzed in vivo when injected in a mammal and transformed into the acid form of the carboxylic acid.

As used herein, "a pharmaceutically acceptable or under food law acceptable carrier medium" includes any and all solvents, diluents, other liquid vehicles, dispersion or suspension aids, surface active ingredients, preservatives, solid binders, lubricants, and the like, as suited to the particular dosage form desired. Remington's Pharmaceutical Sciences, Fifteenth Edition, E. W. Martin (Mack Publishing Co., Easton Pa. 1975) discloses various vehicles or carriers used in formulating pharmaceutical compositions and known techniques for the preparation thereof. Except insofar as any conventional carrier medium is incompatible with the compounds of the invention, (such as by producing any undesirable biological effect or otherwise interacting in a deleterious manner with any other component(s) of the pharmaceutical composition), its use is within the scope of the invention.

The Invention

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Several documents are cited throughout the text of this specification. Each of the documents herein (including any manufacturer's specifications, instructions etc.) are hereby incorporated by reference; however, there is no admission that any document cited is indeed prior art of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions.

It is to be understood that the terms so used are interchangeable under appropriate circumstances and that the embodiments of the invention described herein are capable of operation in other orientations than described or illustrated herein.

It is to be noticed that the term "comprising" used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to the devices consisting only of components A and B. It means that with respect to the present invention, the only relevant components of the device are A and B.

Reference throughout this specification to "one embodiment" or "an embodiment" means that a particular feature, structure or characteristic described in connection with the embodiments is included in at least one embodiment of the present invention. Thus, appearances of the phrases "in one embodiment" or "in an embodiment" in various places throughout this specification are not necessarily all referring to the same embodiments, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Other embodiments of the invention will be apparent to those skilled in the art from consideration of the specification and practice of the invention disclosed herein.

It is intended that the specification and examples be considered as exemplary only.

Each and every claim is incorporated into the specification as an embodiment of the present invention. Thus, the claims are part of the description and are a further description and are in addition to the preferred embodiments of the present invention.

Each of the claims set out a particular embodiments of the invention.

In accordance with the purpose of the invention, as embodied and broadly described herein, the invention is broadly drawn to provide for an enteral or parenteral composition comprising 1) a carboxylic acid and 2) a chemical energy providing macronutrient or caloric organic compound of the group consisting of amino acid, peptide, protein, fatty acid, glycerol, glyceride, triglyceride, monosaccharide, disaccharide, oligosaccharide and polysaccharide or combination thereof for use in the treatment of the physical condition of patient with a disorder of the group consisting of sepsis, severe sepsis, severe sepsis with septic shock, critical illness myopathy and critical illness polyneuropathy.

Exemplary carboxylic acids are acetoacetic acid, lactic acid, propionic acid, 3-hydroxypropanoic acid, malonic acid, hydroxypentanoic acid, butyric acid, β-methylbutyric acid, β-hydroxy β-methylbutyric acid, erythrose, threose, 1,2-butanediol, 1,3-butanediol, 2,3-butanediol, 1,4-butanediol, hydroxybutyric acid, 3-hydroxybutyric acid, L-β-hydroxybutyric acid, D-β-hydroxybutyric acid, DL-β-hydroxybutyric acid or a pharmaceutically acceptable or under food law acceptable salt or a pharmaceutically acceptable or under food law acceptable ester thereof. In a preferred embodiment the carboxylic acid is selected from the group consisting of acetoacetic acid, hydroxybutyric acid, 3-hydroxybutyric acid and L-p-hydroxybutyric acid or a pharmaceutically acceptable or under food law acceptable salt or a pharmaceutically acceptable or under food law acceptable ester thereof.

In a more particular embodiment the carboxylic acid is acetoacetic acid (also diacetic acid); the organic compound with the formula CH3COCH2COOH. It is the simplest beta-keto acid group, and like other members of this class it is unstable. The methyl and ethyl esters, which are quite stable, are produced on a large scale industrially as precursors to dyes. Acetoacetic acid is a weak acid. It is of biochemical importance in various animals, including humans, as one of the endogenous ketone bodies produced by the liver when it breaks down fatty acids into Acetyl-CoA and TCA cycle intermediates are depleted (particularly oxaloacetate, which is formed from pyruvate derived from glycolysis). It can be viewed as the product of joining two acetic acid molecules via a condensation reaction that ejects a water molecule in the process, although that is only one of the ways of forming the acetoacetate molecule. In the human body, a large portion of acetoacetate is converted to beta-hydroxybutyrate, a rich energy source for the brain, which cannot run directly on fatty acids themselves due to their poor ability to cross the blood-brain barrier. In the mammalian body, a large portion of acetoacetate is converted to beta-hydroxybutyrate.

In yet another particular embodiment the carboxylic acid is β-Hydroxybutyric acid, also known as 3-hydroxybutyric acid, an organic compound and a beta hydroxy acid with the formula CH3CH(OH)CH2CO2H; its conjugate base is beta-hydroxybutyrate, also known as 3-hydroxybutyrate. β-Hydroxybutyric acid is a chiral compound having two enantiomers, D-β-hydroxybutyric acid and L-β-hydroxybutyric acid. Its oxidized and polymeric derivatives occur widely in nature.

In one embodiment the enteral or parenteral composition is intended for use in the treatment for preventing or improving muscle weakness of patient with a disorder of the group consisting of sepsis, severe sepsis, severe sepsis with septic shock, critical illness myopathy and critical illness polyneuropathy. In other embodiments the enteral or parenteral composition is intended for use in the treatment for preventing or improving muscle weakness, despite muscle wasting of a patient with a disorder of the group consisting of sepsis, severe sepsis, severe sepsis with septic shock, critical illness myopathy and critical illness polyneuropathy.

In yet another embodiment of the invention, the composition is used without causing or without aggravating a hepato-pancreato-biliary disorder. In a more particular embodiment the composition is used without causing or without aggravating fatty liver.

In other embodiment of the invention the enteral or parenteral composition further comprises a pharmaceutically acceptable or under food law acceptable carrier.

In one embodiment of the invention the enteral or parenteral composition has a total calorie content between 16-106% of the calculated caloric target for intensive care (ICU) patients.

In one embodiment of the invention the enteral or parenteral composition has a total calorie content between 200 to 2000 kcal/1, yet more preferable between 900 to 1400 kcal/1, yet more preferable 900 to 1300 kcal/1, 1100 to 1200 kcal/l.

In another particular embodiment, the composition has a calorie content of monosaccharide, disaccharide, oligosaccharide, polysaccharide, fatty acid, glycerol, glyceride and/or triglyceride between 600 to 1300 kcal/1, yet more preferable between 700 to 1200 kcal/1, yet more preferable 800 to 1100 kcal/1, 900 to 1000 kcal/1. In another particular embodiment the composition has a calorie content of amino acid, peptide and/or protein between 20 to 330 kcal/1, yet more preferable between 50 to 300 kcal/1, yet more preferable 100 to 250 kcal/1 and most preferable 150 to 200 kcal/1.

In yet another particular embodiment, the composition has a calorie content of monosaccharide, disaccharide, oligosaccharide and/or polysaccharide between 200 to 800 kcal/1, yet more preferable between 300 to 800 kcal/1, yet more preferable 400 to 700 kcal/l and most preferable 500 to 600 kcal/l.

In yet another particular embodiment, the composition has a calorie content of fatty acid, glycerol, glyceride and/or triglyceride between 200 to 600 kcal/1, yet more preferable between 250 to 550 kcal/l, yet more preferable 300 to 500 kcal/l and most preferable 350 to 450 kcal/l.

In another embodiment the fatty acid, glycerol, glyceride and/or triglyceride provide between 20 to 80%, yet more preferable 25 to 45% and most preferable 30 to 40% of the total calorie content of said composition.

In certain embodiments the carboxylic acid or carboxylate thereof or pharmaceutically acceptable or under food law acceptable salt or a pharmaceutically acceptable or under food law acceptable ester thereof is administered to a patient at a daily dose of about 1.6 mmol/kg to 79.3 mmol/kg, preferably of about 1.6 mmol/kg to 31.7 mmol/kg, more preferably of about 3.2 mmol/kg and the additional chemical energy providing macronutrient or caloric organic compound is administered to a patient at a dose of 10-100% of the calculated caloric target for ICU patients.

In more particular embodiments this administration is enteral or parenteral, once to several times for one day to several days and in 84% of the patients less than 14 days.

In certain embodiments the composition is used in a treatment of a patient with a BMI under 24.9, more particularly in a treatment of a normal weight patient with a BMI between 18.5 and 24.9 or in the treatment of an underweight patient with a BMI under 18.5.

In one aspect, the present invention provides a method for preventing and treating sepsis, severe sepsis, severe sepsis with septic shock, critical illness myopathy and critical illness polyneuropathy. The method comprises administering the enteric or parenteral composition comprising 1) a carboxylic acid and 2) a chemical energy providing macronutrient or caloric organic compound of the group consisting of amino acid, peptide, protein, fatty acid, glycerol, glyceride, triglyceride, monosaccharide, disaccharide, oligosaccharide and polysaccharide or combination thereof. The carboxylic acid can be selected from the group consisting of acetoacetic acid, lactic acid, propionic acid, 3-hydroxypropanoic acid, malonic acid, hydroxypentanoic acid, butyric acid, β-methylbutyric acid, β-hydroxy β-methylbutyric acid, erythrose, threose, 1,2-butanediol, 1,3-butanediol, 2,3-butanediol, 1,4-butanediol, hydroxybutyric acid, 3-hydroxybutyric acid and L-β-hydroxybutyric acid or a pharmaceutically acceptable or under food law acceptable salt or a pharmaceutically acceptable or under food law acceptable ester thereof. In a preferred embodiment the carboxylic acid is selected from the group consisting of acetoacetic acid, hydroxybutyric acid, 3-hydroxybutyric acid and L-β-hydroxybutyric acid or a pharmaceutically acceptable or under food law acceptable salt or a pharmaceutically acceptable or under food law acceptable ester thereof.

The caloric target can be calculated as the caloric need times the Corrected Ideal Body Weight. The formula for calculating Ideal Body Weight for a female patient is 45.5+[0.91×(height in cm−152.4)] and for a male patient 50+[0.91×(height in cm−152.4)]. If BMI<18.5, the Corrected Ideal Body Weight is (Ideal Body Weight+Actual Body Weight)/2, if 27≥BMI≥18.5, the Corrected Ideal Body Weight is the Ideal Body Weight, if BMI>27, the Corrected Ideal Body Weight is the Ideal Body Weight×1.2. The caloric need for a female patient>60 years is 24 kcal/kg/day, the caloric need for a male patient>60 years is 30 kcal/kg/day, the caloric need for a female patient≤60 years is 30 kcal/kg/day, the caloric need for a male patient≤60 years it is 36 kcal/kg/day.

In other embodiments the invention includes method for the treatment for preventing or improving muscle weakness of patient with a disorder of the group consisting of sepsis, severe sepsis, severe sepsis with septic shock, critical illness myopathy and critical illness polyneuropathy, comprising administering an enteric or parenteral composition.

In yet another embodiments the invention includes method for the treatment for preventing or improving muscle weakness of patient despite muscle wasting with a disorder of the group consisting of sepsis, severe sepsis, severe sepsis with septic shock, critical illness myopathy and critical illness polyneuropathy, comprising administering an enteric or parenteral composition.

In certain embodiments the method is used in a treatment of a patient with a BMI under 24.9, more particularly in a treatment of a normal weight patient with a BMI between 18.5 and 24.9 or in the treatment of an underweight patient with a BMI under 18.5.

In certain embodiments the method further comprises one or more pharmaceutically acceptable or under food law acceptable adjuvants, carriers, excipients, and/or diluents.

Particular and preferred aspects of the invention are set out in the accompanying independent and dependent claims. Features from the dependent claims may be combined with features of the independent claims and with features of other dependent claims as appropriate and not merely as explicitly set out in the claims.

Thus, the claims following the detailed description are hereby expressly incorporated into this detailed description, with each claim standing on its own as a separate embodiment of this invention.

EXAMPLES

This invention can be further illustrated by the following examples of preferred embodiments thereof, although it will be understood that these examples are included merely for purposes of illustration and are not intended to limit the scope of the invention unless otherwise specifically indicated.

Materials and Methods

Set-Up of the Animal Model
Diet-induced obesity: Male, 12-week old C57BL/6J mice (Janvier SAS Chassal, France) received ad libitum standard chow (10% fat, E15745-04, ssniff, Soest, Germany), or ad libitum high-fat diet (45% fat, E15744-34, ssniff) for 12 weeks. Body weight was quantified weekly. Only animals placed on the high-fat diet that reached a body weight above 30 g but below 45 g (to avoid morbid obesity-associated metabolic alterations) within the 12 weeks of diet were included in the study. Tail blood glucose measurements indicated that all mice remained normoglycemic during the obesity-inducing diet (Accu-check, Roche, Basel, Switzerland).

Mice experiment 1: At 24 weeks of age, lean and obese animals were randomly allocated to "healthy control" (lean healthy mice (n=8) and obese healthy mice (n=9)) or to "CLP." CLP groups were randomly subdivided into a fasted-CLP or fed-CLP group. The CLP-induced septic critical illness model and nutritional protocols of the animals have previously been described in detail (Marques et al, 2013 Crit Care 17(5):R193). Total body, fat and fat-free mass were quantified with DEXA scans at the start (day −2) and at the end of the 5-day experiment. After 5 days of critical illness, animals were sacrificed by decapitation, vital organs were removed, snap frozen in liquid nitrogen and stored at −80° C., or preserved in paraformaldehyde. In lean CLP animals, 9/15 fasted and 7/11 fed mice survived until day 5. In obese CLP animals, 9/10 fasted and 10/18 fed mice survived until day 5.

Mice experiment 2: We examined muscle force ex vivo in lean and diet-induced obese CLP mice. The experimental setup was comparable to that of mice experiment 1. Mice were randomly allocated to "healthy control" or "CLP." As in experiment 1 we had observed that muscle wasting occurred irrespective of feeding, we now only compared parenterally fed with pair-fed lean (n=17) and obese (n=15) healthy mice. Until day 5, 15/18 lean and 15/18 obese CLP mice survived. After 5 days, animals were deeply anesthetized and the m. extensor digitorum longus (EDL) was carefully dissected from both hind limbs for ex vivo muscle force measurements.

Mice Body and Tissue Composition and Mass

To control for potential illness- or resuscitation-related changes in fluid content, dry weight of isolated tissues was obtained by a freeze-drying process. Myofiber cross-sectional area (CSA) was quantified on digital microscopy images of hematoxylin and eosin stained paraffin sections with in-house designed algorithms. In addition, the presence of myofiber degeneration, necrosis and inflammation was histologically evaluated. Triglyceride content of tissues was determined with a commercial colorimetric assay (triglyceride quantification kit, Abcam, Cambridge, UK).

Mice Circulating Fatty Acids, Glycerol and Ketone Bodies

Serum concentrations of free fatty acids, glycerol and 3-hydroxybutyrate (3-HB) were determined with commercially available assay kits (free fatty acid fluorometric assay kit, Cayman Chemical Company, Ann Arbor, MI, USA; glycerol assay kit, Sigma-Aldrich, Saint Louis, MO, USA; EnzyChrom ketone body assay kit, BioAssay Systems, Hayward, CA, USA).

Mice Tissue Gene Expression and Protein Expression Analyses

Messenger RNA of skeletal muscle and liver was isolated and cDNA was quantified in realtime as previously described with commercial TaqMan® Assays (Applied Biosystems, Carlsbad, CA, USA). Data were normalized to ribosomal 18S (Rn18s) gene expression and expressed as fold change of the mean of the controls. Microtubule-associated protein 1A/1B-light chain 3 (LC3)-I, LC3-II (Ab from Sigma-Aldrich) and p62 protein (Ab from Novus, Littleton, CO, USA) levels were quantified in m. gastrocnemius with Western blots. Data were expressed relative to the means of the controls. Commercial kits were used to measure proteasome (20S-proteasome activity assay, InnoZyme) and cathepsin B/L activities (Cathepsin L activity kit, Millipore, Merck KGaA, Darmstadt, Germany) in m. tibialis anterior homogenates.

Patient Studies

Myofiber CSA: In vivo skeletal muscle needle biopsies were obtained from the m. vastus lateralis of the m. quadriceps femoris of ICU patients on day 8±1 of ICU stay (Casaer M et al, 2011 NEJM 365(6):506-17; Hermans G et al, 2013 Lancet Respir Med 1(8):621-9). As healthy references, in vivo m. vastus lateralis needle biopsies (n=20) were available from healthy individuals undergoing minor urological intervention or surgery for inguinal herniation. Healthy volunteers had comparable demographics as ICU patients. From 122 patients of whom myofiber CSA were available (Hermans et al, 2013 Lancet Respir Med 1(8):621-9), we selected 51 lean patients (BMI≤525 kg/m2) and 51 overweight/obese patients (BMI>25 kg/m2), matched with use of propensity scores obtained by logistic regression (one-to-one nearest neighbor matching without replacement and with a caliper of 0.2). For this propensity score matching, the following baseline characteristics were used: gender, age, presence of malignancy, diabetes, APACHE II score on admission, and randomization. Next, we investigated postmortem m. rectus abdominis skeletal muscle biopsies, harvested immediately after death, from which myofiber CSA was available (Derde S et al, 2012Crit Care Med 40(1):79-89). From 148 available biopsies, 43 lean and 43 overweight/obese patients were propensity score matched similarly as the first set. As healthy references, in vivo m. rectus abdominis biopsies (n=11) were available from non-critically ill individuals with comparable demographics.

Muscle weakness: In fully cooperative patients, who were still in the ICU on day 8±1, muscle strength was quantified with the MRC sum score (Hermans et al, 2013 Lancet Respir Med 1(8):621-9). To correct for a possible bias by an effect of the randomized intervention on ICU stay, a random sample of patients discharged from the ICU was assessed in the regular hospital ward on post-randomization day 8±1. Clinically relevant weakness was diagnosed when the MRC sum score was lower than 48. Of the 352 patients that were tested on post-admission-day 8±1, 139 lean and 139 overweight/obese patients were propensity score matched, similarly as the first sets. Of the 139 lean patients, 74 patients were tested on the regular hospital ward, 65 in the ICU. Of the 139 overweight/obese patients, 76 patients were tested on the ward, 63 in the ICU.

Statistics

Normally distributed data were compared with one-way analysis of variance (ANOVA) with post hoc Fisher's LSD test for multiple comparisons. Not-normally distributed data were analyzed with parametric tests after log- or (double) square root-transformation if this resulted in a normal distribution. Comparison of proportions was performed using Fisher's exact tests. Continuous non-normally distributed data were compared with non-parametric Mann-Whitney U tests. Two-sided p-values≤0.05 were considered statistically significant (Statview 5.0.1, JMP 8.0.1 and SPSS 22 were used). Data are presented as box plots with median, interquartile ranges and 10th and 90th percentiles or as bars with whiskers, representing means and standard error of the mean (SEM). ANOVA or Mann-Whitney p-values are presented in figure legends. Post-hoc p-values<0.1 are plotted on the figures.

Study Approval

All animals were treated according to the Principles of Laboratory Animal Care (U.S. National Society for Medical Research) and the Guide for Care and Use of Laboratory Animals (National Institutes of Health). The protocols for these animal studies had been approved by the Institutional Ethical Committee for Animal Experimentation (project number P051/2010 and P050/2015). The study protocol of the human studies had been approved by the Institutional Review Board of the KU Leuven (ML1820, ML2707, ML4190, ML1094). Written informed consent was obtained from the patients' closest family member and from healthy volunteers.

Example 1: Mice Study—Body Composition

We hypothesized that during critical illness, fat mobilized from excess adipose tissue can provide energy to vital organs more efficiently than exogenous macronutrients, and that this might prevent lean tissue wasting. We tested this hypothesis in a centrally-catheterized mouse model of cecal ligation and puncture (CLP)-induced septic critical illness and in a human study. In lean and premorbidly obese mice, the effect of 5 days of critical illness on body weight and composition, muscle wasting and weakness was compared, each with fasting and parenteral feeding. Additionally, in matched lean and overweight/obese critically ill patients, we compared markers of muscle wasting in muscle biopsies of two muscle groups (musculus (m.) vastus lateralis and m. rectus abdominis) as well as muscle strength, quantified by the Medical Research Council (MRC) sum score.

Prior to CLP, body weight was significantly higher in obese than in lean mice (35.3±0.5 g vs. 29.4±0.6 g, p<0.0001). This was attributable to a higher fat mass in obese compared to lean mice (9.0±0.6 g vs. 4.7±0.2 g, p<0.0001), whereas fat-free mass was equal in obese and lean mice (23.5±0.4 g vs. 22.7±0.4 g, p=0.2).

After 5 days of CLP-induced critical illness, all animals lost a comparable amount of body weight, hence body weight remained higher in obese vs. lean CLP mice (FIG. 1a-b). Critical illness also resulted in loss of fat mass, but obese CLP mice lost more than double the amount of fat mass over 5 days of illness than lean CLP mice (FIG. 1c-d). In both lean and obese CLP mice, the loss of body weight and fat mass was unaffected by parenteral feeding (FIG. 1).

Critical illness resulted in a loss of lean tissue in lean, but not in obese mice, as demonstrated by the reduction in dry weight of isolated m. tibialis anterior and m. soleus (FIG. 2a-b). This coincided with a reduced myofiber CSA of the m. tibialis anterior in the lean, but not in obese CLP mice (FIG. 2c). Consequently, mean muscle myofiber size was larger in obese CLP mice than lean CLP mice (FIG. 2c). Fasting during critical illness tended to further reduce the dry muscle weight (FIG. 2a-b), whereas the occurrence of smaller myofibers was present in both fed and fasted animals (FIG. 2c).

Example 2: Mice Study—Markers of Skeletal Muscle Atrophy and Autophagy

We investigated whether less activation of atrophy pathways could explain the observed preservation of muscle mass and muscle fiber size in obese CLP mice. Compared to lean healthy control mice, muscle protein content tended to be reduced in lean fed CLP mice (83.9±8.3 µg/mg vs. 55.1±10.1 µg/mg, p=0.06) and was reduced in lean fasted CLP mice (50.4±11.1 µg/mg, vs. lean healthy controls, p=0.01). In contrast, obese CLP mice preserved their muscle protein content (108.1±20.8 µg/mg vs. 76.1±14.8 µg/mg in fed CLP mice p=0.8, and 63.5±6.6 µg/mg in fasted CLP mice p=0.1). Gene expression of markers of the ubiquitin-proteasome system, Fbxo32 and Trim63, were upregulated in lean and obese CLP mice (FIG. 3a-b). Fasted lean CLP mice displayed a further increase in Fbxo32 and Trim63 expression (FIG. 3a-b). Activity of the proteolytic enzyme 20S-proteasome was unaffected by critical illness (FIG. 3c). In contrast, cathepsin activity was increased in lean CLP mice, whereas this increase tended to be attenuated in obese CLP mice (FIG. 3d). Compared to lean and obese healthy control animals, fasting further increased the cathepsin activity both in lean and obese CLP mice (FIG. 3d).

Gene expression of Atg7 was elevated in both lean and obese CLP mice, but most pronounced in fasted lean CLP mice (FIG. 3e). In contrast, Atg5 gene expression was only increased in fasted lean CLP mice (FIG. 3f). The LC3 protein ratio (LC3-II/LC3-1), a marker of autophagosome formation, appeared unaffected after 5 days of critical illness (FIG. 3g). Protein levels of p62, used as a marker of insufficiently activated autophagy, were elevated in CLP mice, irrespective of obesity or whether the mice were fasted or received parenteral feeding (FIG. 3h).

To exclude the involvement of increased fibrosis or myostatin-associated hypertrophy in the preservation of muscle mass, we quantified gene expression of fibrogenic genes Col1a1 and S100a4, muscle growth inhibiting factor Mstn, and hypertrophy marker Igf1. These markers were largely unaffected by illness. However, fasted lean CLP mice demonstrated lower Col1a1 and higher Mstn gene expression levels than healthy mice and fasted obese CLP mice. Histological analysis of the muscle in lean and obese CLP mice indicated similar signs of fibrosis (63% and 71% respectively, p=0.6) and fasciitis (11% and 6% respectively, p=0.8). Also structural abnormalities (58% and 65% respectively, p=0.6) and signs of necrosis (16% and 6% respectively, p=0.3) were equally observed in lean and obese CLP mice.

Example 3: Mice Study—Ectopic Triglyceride Content

To determine whether an effect on lipid content might contribute to the preservation of muscle mass in obese CLP mice, muscle triglyceride content was quantified. Whereas healthy lean and obese mice had comparable muscle triglyceride contents, muscle triglyceride content was decreased in lean CLP mice, irrespective of nutritional intake (FIG. 4a). In contrast, triglyceride content of the muscle was preserved in fed and fasted obese CLP mice (FIG. 4a). Furthermore, muscle mass of m. tibialis anterior correlated significantly with muscle triglyceride content (R=0.498, p=0.0002).

Next, we investigated whether a comparable effect was present in the liver. Healthy lean and obese mice had comparable hepatic triglyceride contents (FIG. 4b), confirming the absence of potentially adverse features of a morbid obesity-associated liver steatosis. Liver triglyceride content was decreased in lean CLP mice, irrespective of nutritional intake, whereas it was preserved in fed and fasted obese CLP mice (FIG. 4b).

Example 4: Mice Study—Markers of Fatty Acid and Glycerol Metabolism

The observations of enhanced loss of fat mass (FIG. 1b) and preservation of ectopic (muscle and liver) fat (FIG. 4) in obese CLP mice, suggest that during CLP-induced critical illness, more fat was mobilized from the adipose tissue of obese CLP mice. Therefore, we subsequently quantified circulating levels of fatty acids and glycerol and markers of hepatic uptake and metabolism of these substrates. Serum fatty acid concentration was not different from controls in lean CLP mice. In contrast, in obese CLP mice, fatty acid serum concentration was decreased (obese healthy control mice 1384.4±221.3 µM vs. obese CLP mice 804.9±76.8 µM; p=0.007) (FIG. 5a). Hepatic gene expression of Cd36, a fatty acid transporter, was markedly increased in obese (healthy, fasted-CLP and fed-CLP) mice compared to lean (healthy, fasted-CLP and fed-CLP) mice (FIG. 5b). Hepatic gene expression of Acadl, the first enzyme of β-oxidation, was comparable in lean, obese, healthy, and CLP mice (data not shown). However, hepatic gene expression of Hmgcs2, encoding for the mitochondrial enzyme that catalyzes the first step of ketogenesis, decreased in lean CLP animals (lean healthy control mice 1.0±0.1 vs. lean CLP mice 0.6±0.1; p=0.01), whereas its expression was unaltered in obese CLP mice (FIG. 5c). Thus, obese CLP mice showed higher Hmgcs2 gene expression than lean CLP mice. This difference in gene expression coincided with higher serum ketone body (3-HB) concentrations in obese CLP mice than in lean CLP mice (FIG. 5d).

Figure 6C:
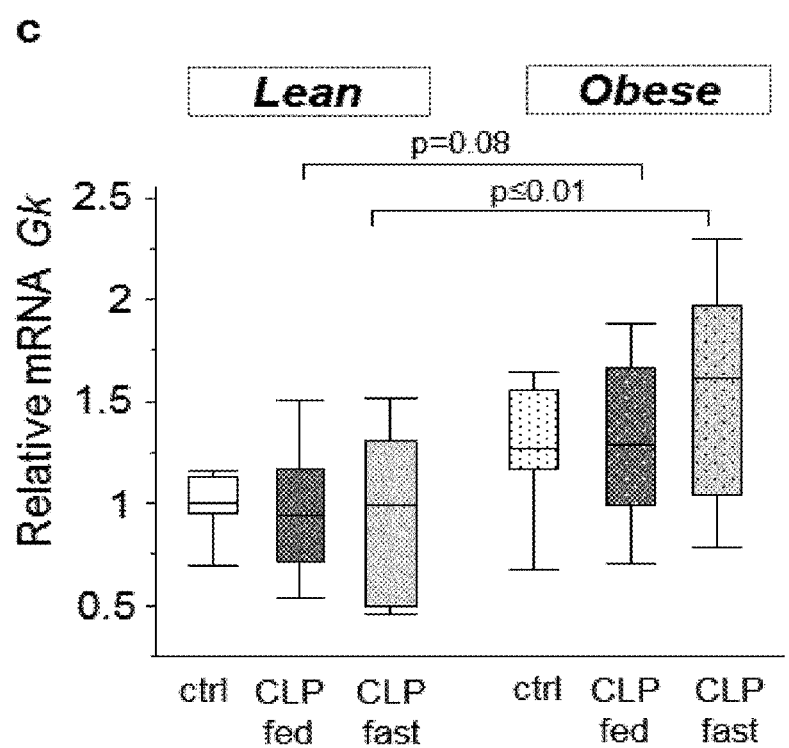
FIG. 6 Mice glycerol metabolism. (a) Serum glycerol concentrations (ANOVA p<0.01). (b) Relative mRNA levels of Aap9 (ANOVA p=0.4). (c) Relative mRNA levels of Gk (ANOVA p=0.04). Gene expression data are expressed normalized to Rn18s gene expression and as a fold change of the mean of the lean healthy controls. White, healthy lean mice (n=8); dark gray, fed lean CLP mice (n=7); light gray, fasted lean CLP mice (n=9); white dotted, healthy obese mice (n=9); dark gray dotted, fed obese CLP mice (n=10); light gray dotted, fasted obese CLP mice (n=9). [CLP: cecal ligation and puncture, ctrl: healthy control mice, fed: parenterally fed, fast: fasted]

Healthy lean mice had lower serum glycerol concentrations than healthy obese mice. Whereas circulating glycerol was not altered by critical illness in lean mice, glycerol serum concentrations in obese CLP mice were reduced after 5 days of critical illness (FIG. 6a). Gene expression of Aqp9, an aquaglyceroporin membrane channel that conducts glycerol into the liver, was unaltered (FIG. 6b). However, gene expression of Gk, encoding the rate-limiting enzyme in the hepatic conversion from glycerol to glucose, was higher in obese compared to lean mice (FIG. 6c). Overall, these parameters were not affected by the nutritional intake, neither in lean nor in obese CLP mice (FIGS. 5 and 6).

Example 5: Mice Study—Muscle Strength and Recovery from Fatigue

Figure 7C:
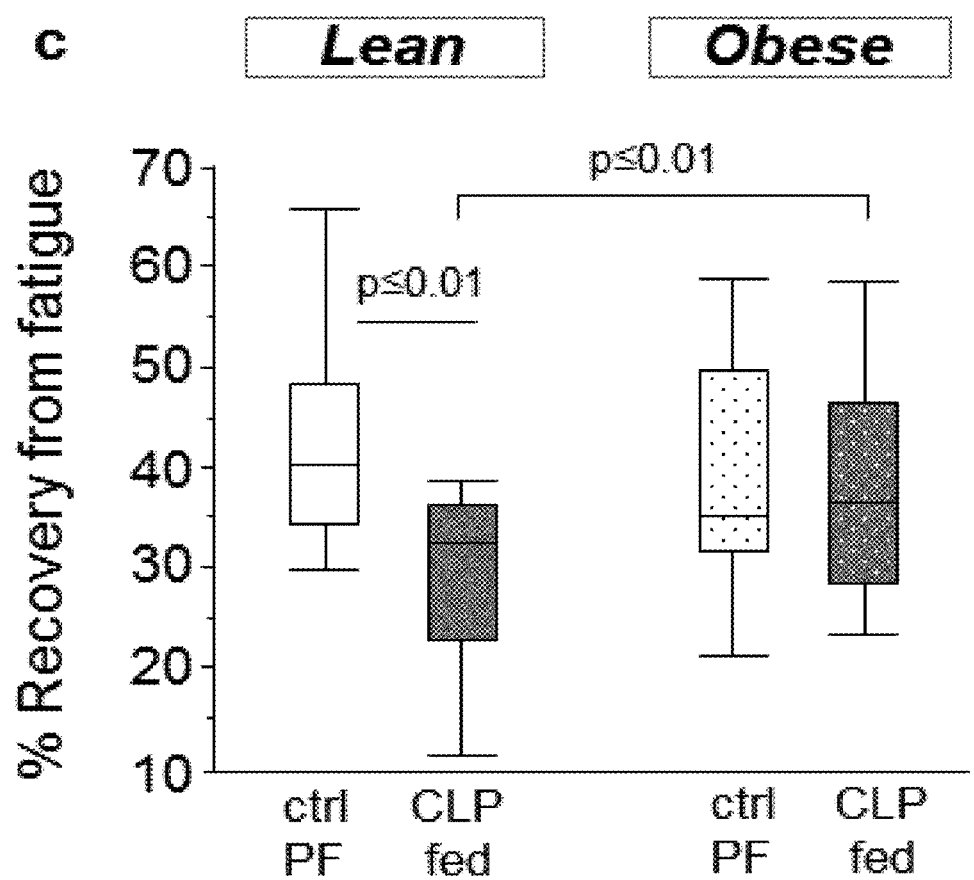
FIG. 7 Mice muscle force. Ex vivo force measurements of the m. extensor digitorum longus (EDL). (a) Dry weight (ANOVA p=0.04). (b) Peak tetanic muscle tensions (ANOVA p≤0.01). (c) Recovery from fatigue after 10 minutes, as percentage of initial muscle force (ANOVA p≤0.01). White, healthy lean mice, pair-fed (n=17); dark gray, fed lean CLP mice (n=15); white dotted, healthy obese mice, pair-fed (n=15); dark gray dotted, fed obese CLP mice (n=15). [CLP: cecal ligation and puncture, ctrl: healthy control animals, PF, pair-fed, fed: parenterally fed]

After 5 days of critical illness, only the lean but not the obese mice lost m. EDL mass (FIG. 7a). Lean and obese healthy control mice had comparable twitch tensions (39.2±1.9 mN vs. 43.9±4.6 mN; p=0.5), tetanic tensions (213.3±9.5 mN vs. 203±15.4 mN; p=0.4) and fatigue recovery rates (42% vs. 38%; p=0.2) (FIG. 7). Peak twitch tension was unaltered in lean and obese CLP mice (data not shown). However, lean CLP mice demonstrated a lower peak tetanic tension and a lower recovery from fatigue than lean control mice, whereas obese CLP mice maintained peak tetanic tensions and the recovery from fatigue was comparable to obese healthy control mice (FIG. 7b-c). Compared to lean CLP mice, obese CLP mice tended to have higher peak tetanic tensions and displayed better recovery from fatigue (FIG. 7b-c).

Example 6: Patient Study—Muscle Wasting and Weakness

We next assessed whether attenuation of muscle wasting and muscle weakness was also present in obese/overweight versus lean prolonged critically ill patients. Myofiber CSA of the m. vastus lateralis was comparable in lean and overweight/obese healthy volunteers. However, myofibers were significantly smaller in lean prolonged critically ill patients than in healthy volunteers, as illustrated by a shift to the left in the histogram of myofiber size distribution (FIG. 8a). In contrast, overweight/obese critically ill patients maintained their myofiber size compared to healthy controls, which resulted in larger myofibers compared to lean critically ill patients (FIG. 8a). These findings were confirmed in a second set of postmortem m. rectus abdominis biopsies (FIG. 8b). Furthermore, fewer overweight/obese prolonged critically ill patients suffered from muscle weakness than lean prolonged critically ill patients (12% vs. 24%: p=0.004).

In examples 1 to 6 we demonstrated in mice and humans that being obese prior to becoming critically ill protected against muscle wasting and weakness. As compared with lean critically ill mice, obese mice showed better preservation of muscle mass and myofiber size, irrespective of whether they were fasted or received parenteral nutrition. Furthermore, obese CLP mice preserved their muscle strength. Obesity, but not nutrition during critical illness, attenuated the loss of lipids and myofibrillary proteins, and increased mobilization and metabolization of fat from adipose tissue. In human muscle biopsies of overweight/obese prolonged critically ill patients, myofiber size appeared more preserved than in lean patients. Moreover, fewer overweight/obese patients suffered from muscle weakness than lean patients, assessed one week after admission to the ICU.

Critical illness is known to induce loss of muscle mass and the development of muscle weakness (Kress J P, Hall J B, 2014 NEJM, 370(17):1626-35). Although multiple mechanisms underlying muscle wasting and weakness during critical illness have been identified, efficient therapies preventing critical illness-associated muscle wasting and weakness remain elusive. Therefore, the finding that obesity not only protected against lean tissue wasting but also against muscle weakness during critical illness is remarkable.

We observed increased markers of the ubiquitin-proteasome and the autophagy-lysosome pathway in muscle of critically ill mice. Obesity tended to attenuate increased cathepsin activity after 5 days of critical illness. Furthermore, whereas in lean critically ill mice, fasting induced a significant further increase in atrophy markers, this fasting response was absent in obese critically ill mice. In addition to the ubiquitin-proteasome pathway, also insufficiently activated autophagy can play a key role in muscle wasting and the development of muscle weakness (Hermans et al, 2013 Lancet Respir Med 1(8):621-9). Insufficient autophagy activation is characterized by elevated p62 protein levels and an inadequate rise in LC3-II/LC3-1 ratio. We observed p62 accumulation in the presence of an unaltered LC3-II/LC3-1 ratio and increased expression of autophagy-related genes Atg5 and Atg7 in muscle of lean and obese CLP mice. Similarly to the findings for the ubiquitin-proteasome pathway, only lean but not obese critically ill animals displayed an additional upregulation in autophagy genes in response to fasting. Histological analysis indicated presence of muscle abnormalities (such as myocyte necrosis, fibrosis and fasciitis) in our mice model consistent with earlier human and rodent observations. However, the histological markers as well as gene expression of fibrogenesis and muscle hypertrophy markers were not affected by the presence of obesity during critical illness, suggesting that these pathways did not contribute to the preservation of muscle mass in obese critically ill mice. The maintenance of muscle proteins and stored ectopic (muscle and liver) triglycerides in obese CLP mice suggests that obese mice, in contrast to lean mice, may use other energy stores during critical illness. The observation that total body fat mass was more reduced during critical illness in obese compared to lean mice, concomitantly with the preservation of ectopic fat, indicates that more lipids were released from adipose tissue stores of obese CLP mice. Theoretically, sufficiently available circulating fatty acids and glycerol for energy consumption would reduce the need for utilization of energy substrates stored in vital organs, such as structural lipids and proteins. However, obese CLP mice did not display higher circulating fatty acids and free glycerol than lean CLP mice. Possibly, we missed a rise in circulating lipids on an earlier time point. On the other hand, obesity has been shown to influence the turnover rate of circulating fatty acids and glycerol, and thus increased metabolization of these substrates by the liver could have decreased their serum concentrations. In our mouse study we indeed observed such signs of an elevated fatty acid and glycerol turnover rate in all obese mice, unaffected by nutrition or illness. The increase in circulating ketone bodies in obese CLP mice further indicates enhanced fatty acid metabolism. Obese mice thus appear to have a different metabolic response to prolonged critical illness as compared with lean mice. Together, our findings may suggest that obese critically ill mice preferentially use fat from adipose tissue, while lean critically ill mice may utilize ectopically stored lipids and proteins. Possibly, the combination of mobilizing excess stored triglycerides in adipose tissue, and enhanced metabolism of fatty acids and glycerol from these stores, prevents or decreases the use of stored proteins and triglycerides in muscle tissue during critical illness. Glycerol and fatty acid metabolism can indeed generate vital energy through the production of glucose and ketone bodies. In addition, ketone bodies may also directly be involved in the attenuation of muscle wasting, comparable to what has been observed in pancreatic cancer cachexia (Shukla S K et al, 2014 Cancer&Metabolism 2:18).

It was demonstrated earlier that administration of parenteral nutrition to critically ill patients could not attenuate muscle wasting and even aggravated weakness (Hermans et al, 2013 Lancet Respir Med 1(8):621-9; Derde S et al, 2012Crit Care Med 40(1):79-89). Our observations now suggest that the use of endogenous lipids released from the adipose tissue may counteract muscle wasting.

Example 7: Mice Study—Effect of Administration of D,L-3-Hydroxybutyrate

The observation that in contrast to lean mice, obese mice strikingly do not suffer from muscle wasting and weakness when critically ill and they present with higher serum levels of the ketone body 3-hydroxybutyrate during illness, prompted us to assess whether the administration of 3-hydroxybutyrate to lean critically ill mice could prevent muscle wasting and weakness. Within the skeletal muscle, 3-hydroxybutyrate has shown to be effectively used as energy source and was found to improve physical endurance in highly trained athletes. Also, there is evidence that ketone bodies could inhibit muscle atrophy. Therefore, we hypothesized that the administration of 3-hydroxybutyrate to lean critically ill mice could prevent muscle wasting and weakness.

We studied the effect of subcutaneous administration of D,L-3-hydroxybutyrate sodium salt on muscle wasting and weakness in a validated mouse model of prolonged critical illness evoked by sepsis (cecal ligation and puncture followed by resuscitation and intensive medical care). The intervention was studied in the parenterally fed and in the fasted state.

Figure 9:
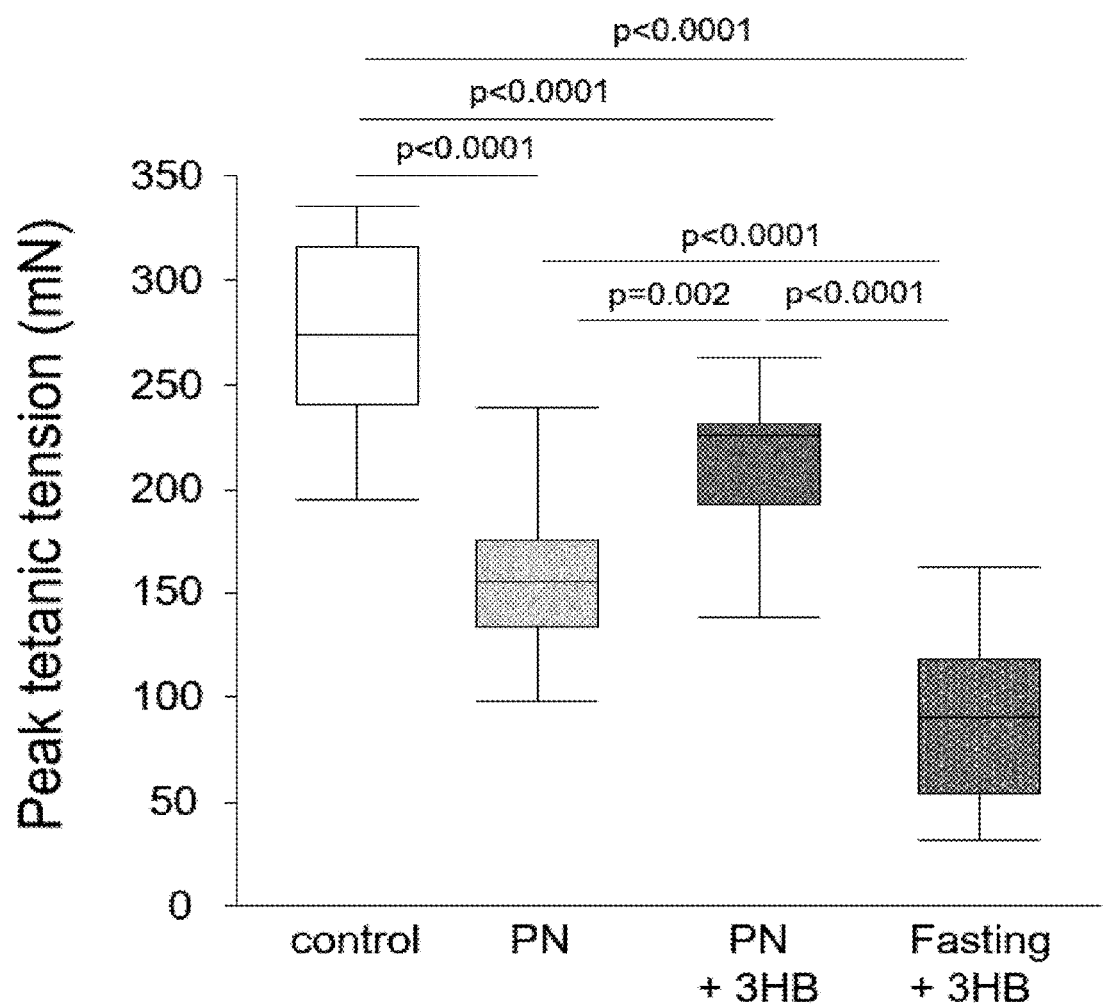
FIG. 9. Effect of 3-hydroxybutyrate administration on muscle weakness in prolonged critically ill mice. Ex vivo force measurements of the extensor digitorum longus (EDL) muscle. White, healthy control mice (n=15); light gray, parenterally fed critically ill mice (n=16); dark gray, parenterally fed critically ill mice receiving daily subcutaneous injections of 3-hydroxybutyrate (n=14); dark gray dotted, fasted critically ill mice receiving daily subcutaneous injections of 3-hydroxybutrate (n=14). [PN=parenteral nutrition; 3HB=3-hydroxybutyrate].
Figure 10:
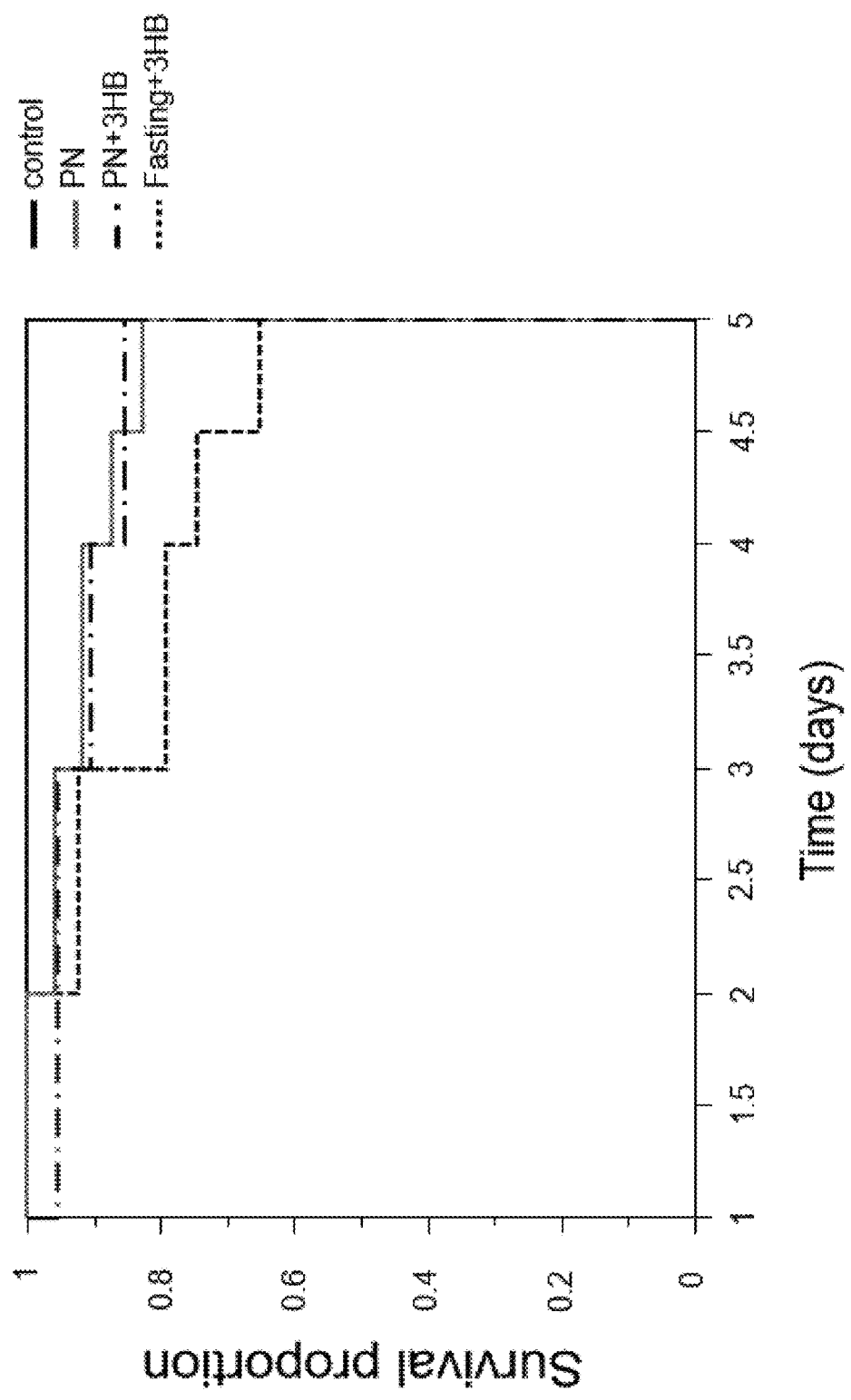
FIG. 10. Effect of 3-hydroxybutyrate injections on 5-day mortality in prolonged critically ill mice. Black line, healthy control mice (15/15 survivors); gray line, parenterally fed critically ill mice (17/20 survivors); dash dot line; parenterally fed critically ill mice receiving 3-hydroxybutyrate (17/21 survivors); dotted line, fasted critically ill mice receiving 3-hydroxybutyrate (14/22 survivors). [PN=parenteral nutrition; 3HB=3-hydroxybutyrate].

Muscle function was quantified in isolated extensor digitorum longus (EDL) muscle. Critical illness in parenterally fed mice (PN) reduced the absolute maximal force generated by EDL to 57% of healthy controls (p<0.0001) (FIG. 9). However, when parenterally fed critically ill mice received subcutaneous twice daily a bolus of 75 mg of D,L-3-hydroxybutyrate sodium salt (PN+3HB), maximal muscle force improved dramatically to 83% of healthy controls (p<0.0001) (FIG. 9). In contrast, in fasted critically ill mice, twice daily D,L-3-hydroxybutyrate sodium salt boluses of 75 mg (fasting+3HB) increased risk of death (FIG. 10) and in survivors reduced maximal muscle force to 33% of the force of healthy control mice (p<0.0001) (FIG. 9).

Figure 11:
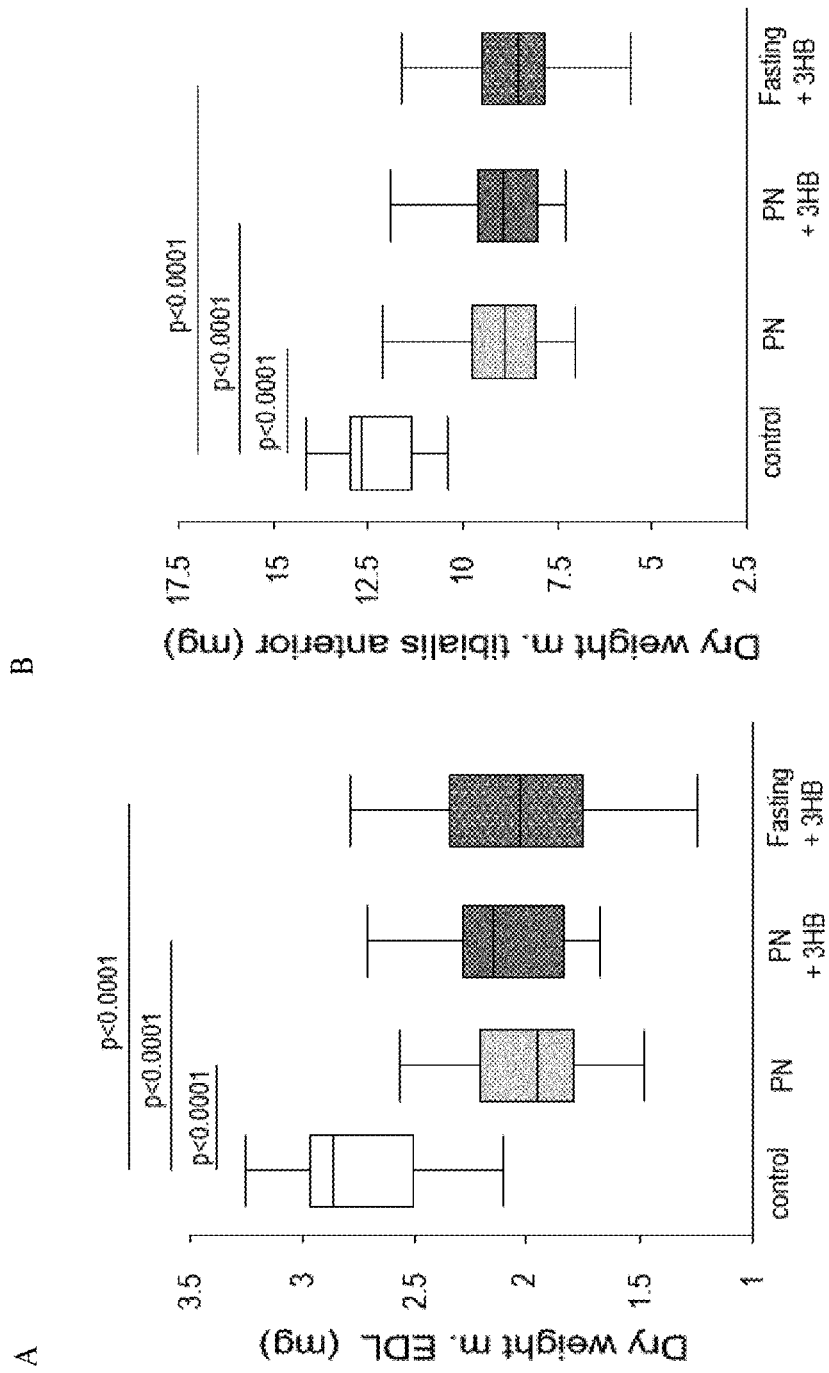
FIG. 11. Effect of 3-hydroxybutyrate administration on muscle wasting in prolonged critically ill mice. (a) Dry weight of the extensor digitorum longus (EDL) muscle. (b) Dry weight of the tibialis anterior muscle. White, healthy control mice (n=15); light gray, parenterally fed critically ill mice (n=17); dark gray, parenterally fed critically ill mice receiving daily subcutaneous injections of 3-hydroxybutyrate (n=17); dark gray dotted, fasted critically ill mice receiving daily subcutaneous injections of 3-hydroxybutrate (n=14). [PN=parenteral nutrition; 3HB=3-hydroxybutyrate].

Muscle wasting was evaluated by quantification of the dry weight of isolated skeletal muscles. Muscle weight of the EDL muscle decreased in all critically ill mice, irrespective of hydroxybutyrate treatment or nutritional regime (1.9±0.3 mg for PN, 2.1±0.3 mg for PN+3HB, and 2.0±0.4 mg for fasting+3HB as compared with 2.7±0.3 mg in healthy control mice; p<0.0001) (FIG. 11A). Also the weight of the larger tibialis anterior muscle decreased significantly in all groups of critically ill mice as compared with healthy controls, again irrespective of hydroxybutyrate treatment and feeding regime (9.0±1.2 mg for PN, 8.9±1.4 mg for PN+3HB, and 8.4±1.8 mg for fasting+3HB versus 12.4±1.3 mg in healthy controls; p<0.0001) (FIG. 11B).

Figure 12:
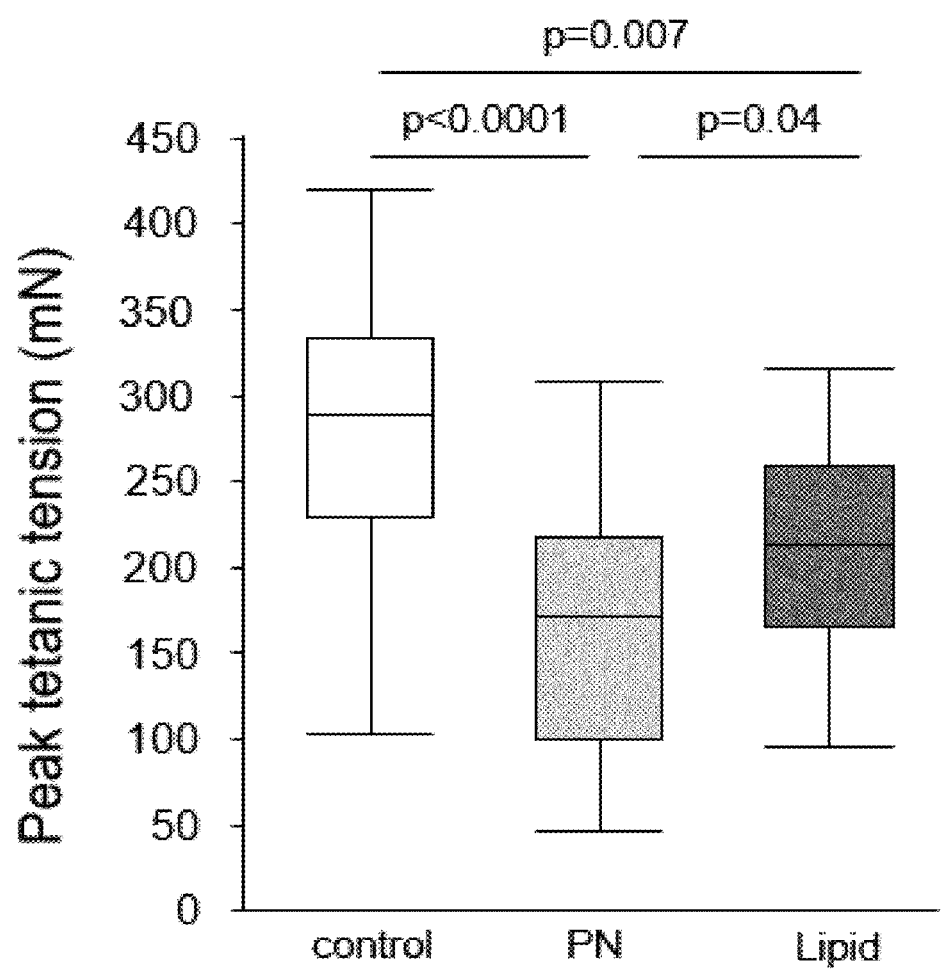
FIG. 12. Effect of a ketogenic diet on muscle weakness in prolonged critically ill mice. Ex vivo force measurements of the extensor digitorum longus (EDL) muscle. White, healthy control mice (n=17); light gray, parenterally fed critically ill mice (n=16); dark gray, critically ill mice on a lipid-rich, ketogenic diet (n=15). [PN=parenteral nutrition; Lipid=lipid-rich, ketogenic diet].
Figure 13A:
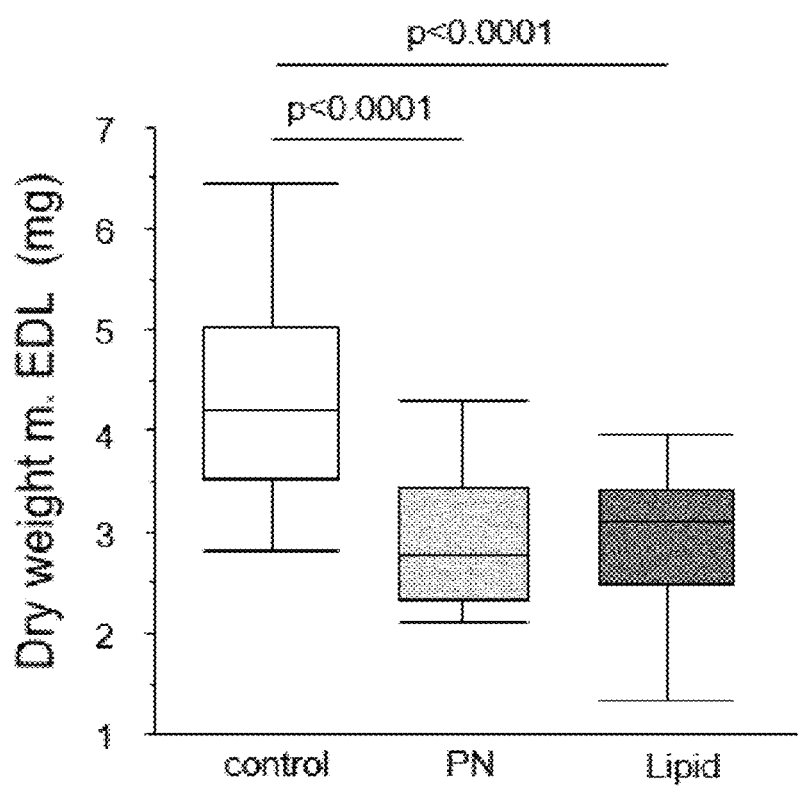
FIG. 13. Effect of a ketogenic diet on muscle wasting in prolonged critically ill mice. (a) Dry weight of the extensor digitorum longus (EDL) muscle. (b) Dry weight of the tibialis anterior muscle. White, healthy control mice (n=24); light gray, parenterally fed critically ill mice (n=23); dark gray, critically ill mice on a lipid-rich, ketogenic diet (n=23). [PN=parenteral nutrition; Lipid=lipid-rich, ketogenic diet].
Figure 13B:
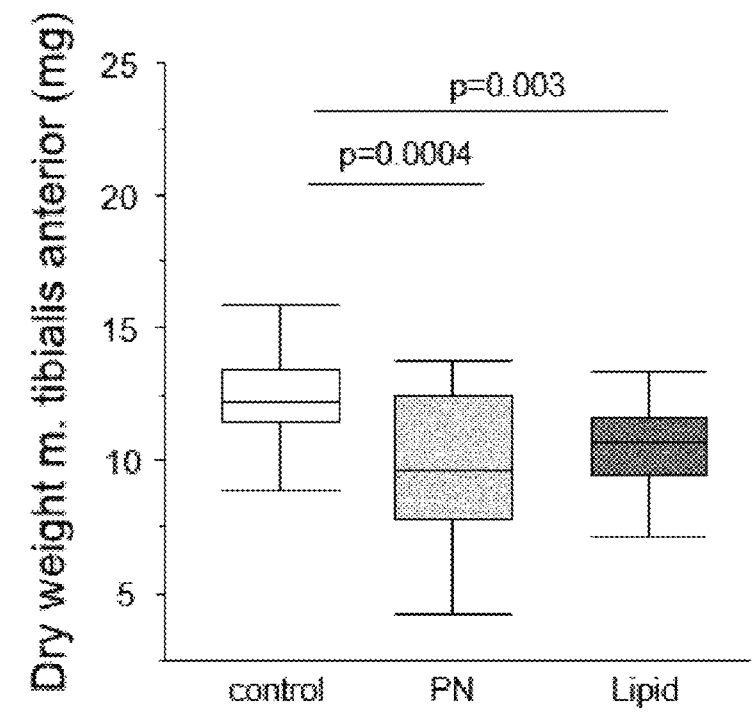
Figure 14:
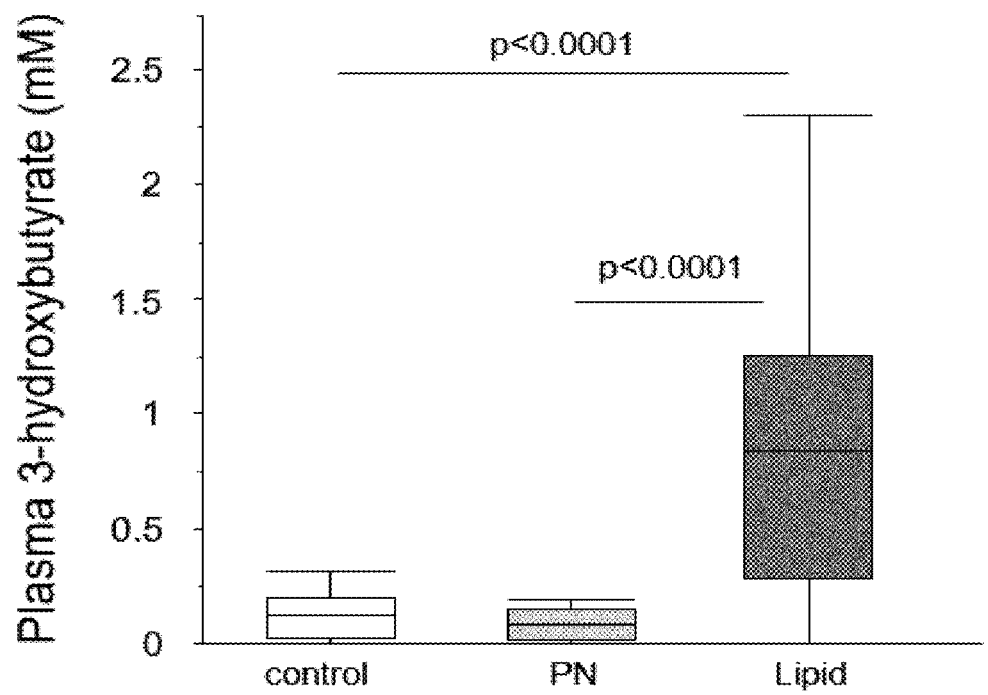
FIG. 14. Circulating 3-hydroxybutyrate in prolonged critically ill mice. White, healthy control mice (n=24); light gray, parenterally fed critically ill mice (n=23); dark gray, critically ill mice on a lipid-rich, ketogenic diet (n=23). [PN=parenteral nutrition; Lipid=lipid-rich, ketogenic diet].
Figure 15:
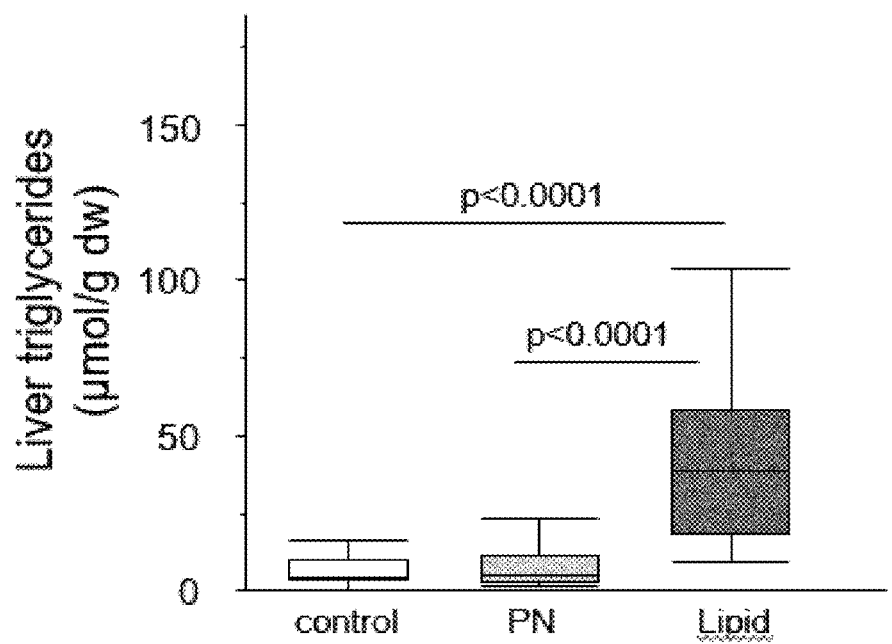
FIG. 15. Effect of a ketogenic diet on liver steatosis in prolonged critically ill mice. Liver steatosis, presented as the hepatic triglyceride content. White, healthy control mice (n=24); light gray, parenterally fed critically ill mice (n=23); dark gray, critically ill mice on a lipid-rich, ketogenic diet (n=23). [PN=parenteral nutrition; Lipid=lipid-rich, ketogenic diet].

In a second experiment we compared the effect of a lipid-rich, ketogenic diet (90% lipids, 10% glucose), with standard PN (35% lipids, 49% glucose, 16% proteins) on muscle wasting and weakness in our mouse model of prolonged critical illness evoked by sepsis. Critical illness in PN mice reduced the absolute maximal force generated by EDL to 58% of healthy controls (p<0.0001), whereas mice on a lipid-rich diet (Lipid) presented with highly improved maximal force to 73% of healthy controls (p=0.04) (FIG. 12). Muscle dry weight of the EDL muscle decreased in all critically ill mice, irrespective of nutritional regime (2.9±0.6 mg for PN, 2.9±0.6 mg for Lipid, as compared with 4.3±1 mg for healthy controls; p<0.0001) (FIG. 13A). Also tibialis anterior dry weight decreased similarly in all critically ill mice (9.6±mg for PN and 10.2±1.8 mg for Lipid versus 12.7±3.4 mg in healthy controls; p<0.001) (FIG. 13B). The lipid-rich diet increased circulating 3-hydroxybutyrate to 0.8±0.6 mM (p<0.0001 compared to PN critically ill mice and healthy controls) (FIG. 14). Adversely, livers of Lipid critically ill mice contained 7-times more triglycerides than PN critically ill mice and healthy controls (p<0.0001) (FIG. 15). This unfavorable liver steatosis limits the therapeutic potential of a lipid-rich, ketogenic diet during critical illness.

In conclusion, daily supplementation of D,L-3-hydroxybutyrate to parenterally fed mice largely prevented muscle weakness but not muscle wasting during prolonged sepsis-induced critical illness. A similar preventive effect on muscle weakness but not wasting was observed with the administration of a lipid-rich diet, but at the cost of unfavorable liver steatosis.

Example 8: Energy Experiment

To investigate whether there is any potential synergy in the effect on muscle weakness of D,L-3-hydroxybutyrate sodium salt (3HB) and the individual macronutrient components of standard parenteral nutrition (lipids, proteins, glucose) we performed an additional animal experiment. We again used our validated mouse model of prolonged (5 days) critical illness evoked by sepsis (cecal ligation and puncture followed by fluid resuscitation and intensive medical care). Critically ill mice received twice daily a bolus injection of 75 mg of 3HB combined either with standard total parenteral nutrition (3HB+TPN, mixture of glucose, lipids and amino acids), a glucose infusion (3HB+GLUC), a lipid-low-glucose infusion (3HBB+LIP), or an amino-acids-low-glucose infusion (3HB+AA) [Table 1 for composition].

Figure 16C:
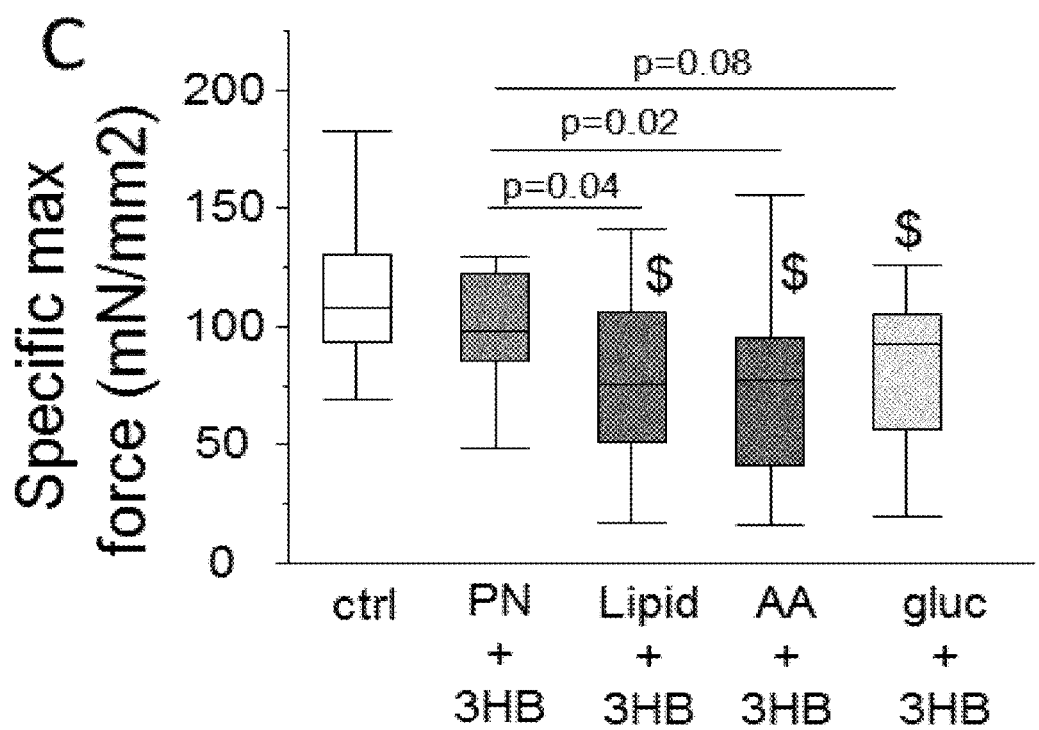
FIG. 16 Effect of ketone supplementation with different compositions of parenteral nutrition on muscle wasting in prolonged critically ill mice. (A) Wet weight of the extensor digitorum longus (EDL) muscle. (B) Ex vivo absolute force measurements of the EDL muscle. (C) Ex vivo specific force measurements of the EDL muscle. White, healthy control mice (n=15); pink, TPN+3HB critically ill mice (n=16); brown, LIPID+3HB critically ill mice (n=16); green, AA+3HB critically ill mice (n=16); blue, GLUC+3HB critically ill mice (n=17). $, p?0.05 different from healthy controls.

Muscle mass and function was quantified in isolated extensor digitorum longus (EDL) muscle. Total EDL muscle weight decreased similarly in all critically ill mice, irrespective of parenteral nutrition composition with which the 3HB was combined (FIG. 16A). In contrast, muscle force was affected differently among the ill groups (FIG. 16B). Mice in the TPN+3HB group reached 76% (212±14 mN) of the maximal muscle force of healthy controls (278±17 mN, p<0.002), similarly to our previous findings. In contrast, the maximal force reached by the GLUC+3HB, LIPID+3HB and AA+3HB groups was significantly lower than the TPN+3HB group (p≤0.05) with respectively 62% (173±13 mN), 57% (158±16 mN) and 56% (155±15 mN) of the maximal muscle force of the healthy controls (p<0.0001). Specific maximal muscle force, corrected for the total EDL weight, was comparable between TPN+3HB and healthy controls, whereas it was lower than controls similarly in the GLUC+3HB, LIPID+3HB and AA+3HB groups (FIG. 16C).

In conclusion, we could confirm that daily supplementation of D,L-3-hydroxybutyrate (3HB) to total parenteral nutrition largely prevented muscle weakness but not muscle wasting during prolonged sepsis-induced critical illness. Importantly, the improvement of muscle weakness with ketone supplementation was only observed when combined with total parenteral nutrition that comprised a balanced mixture of glucose, lipids and amino acids (FIG. 16).

TABLE 1

Composition of the different forms of parenteral nutrition

| Daily dose (mg) | Glucose | Lipids | Amino acids | D,L-3-hydroxybutyrate sodium salt |
|---|---|---|---|---|
| TPN + 3HB | 672 | 192 | 213 | 150 |
| GLUC + 3HB | 672 | — | — | 150 |
| LIPID + 3HB | 298 | 192 | — | 150 |
| AA + 3HB | 298 | — | 213 | 150 |

What is claimed is:

1. A method of treating or preventing muscle weakness in myopathy caused by sepsis in a critically ill intensive care patient, the method comprising administering to the critically ill intensive care patient in need thereof (i) an 3-hydroxybutyrate of the groups consisting of an 3-hydroxybutyrate, its enantiomer (R)-3-hydroxybutyric acid, and (S)-3-Hydroxybutyric acid or enantiomeric mixture, or a pharmaceutically acceptable or under food law acceptable salt, or a pharmaceutically acceptable or under food law acceptable ester thereof, and (ii) a macronutrient comprising glucose, lipids and amino acids.

2. The method according to claim 1, whereby the administering (i) the 3-hydroxybutyrate and (ii) the macronutrient is carried out with a continuous or multiple dose regime at a dose range of 0.08 g/kg patient body weight to 4.13 g/kg patient body weight per 24 hours.

3. The method according to claim 1, wherein the administering (i) the 3-hydroxybutyrate and (ii) the macronutrient is carried out with a continuous or multiple dose regime at a dose range of 0.8 mmol/kg patient body weight to 39.7 mmol/kg patient body weight per 24 hours.

4. The method according to claim 1, wherein the administering (i) the 3-hydroxybutyrate and (ii) the macronutrient is carried out with a continuous or bolus, parenteral or enteral dose range of 0.08 g/kg to 4.13 g/kg patient body weight per 24 hours.

5. The method according to claim 1, wherein the administering (i) the 3-hydroxybutyrate and (ii) the macronutrient is carried out with a continuous or bolus, parenteral or enteral dose range of 0.8 mmol/kg patient body weight to 39.7 mmol/kg patient body weight per 24 hours.

6. The method according to claim 1, wherein the 3-hydroxybutyrate is administered to the critically ill intensive care patient at a daily dose of about 1.6 mmol/kg to 79.3 mmol/kg.

7. The method according to claim 1, wherein the patient has a BMI under 24.9.

8. The method according to claim 6, wherein the daily dose of the 3-hydroxybutyrate is about 1.6 mmol/kg to 31.7 mmol/kg.

9. The method according to claim 6, wherein the daily dose of the 3-hydroxybutyrate is about 3.2 mmol/kg.

\* \* \* \* \*